United States Patent
Wulff et al.

(10) Patent No.: US 11,173,146 B2
(45) Date of Patent: Nov. 16, 2021

(54) SELECTIVE ACTIVATORS OF THE INTERMEDIATE CONDUCTANCE CA2+ACTIVATED K+ CHANNEL KCA3.1 AND THEIR METHODS OF USE

(71) Applicant: The Regents of the University of California, Oakland, CA (US)

(72) Inventors: Heike Wulff, Davis, CA (US); Nichole Coleman, San Francisco, CA (US); Brandon M. Brown, Davis, CA (US); Aida Olivan-Viguera, Saragossa (ES); Ralf Kohler, Saragossa (ES)

(73) Assignee: The Regents of the University of California, Oakland, CA (US)

( * ) Notice: Subject to any disclaimer, the term of this patent is extended or adjusted under 35 U.S.C. 154(b) by 334 days.

(21) Appl. No.: 15/306,457

(22) PCT Filed: Apr. 24, 2015

(86) PCT No.: PCT/US2015/027636
§ 371 (c)(1),
(2) Date: Oct. 24, 2016

(87) PCT Pub. No.: WO2015/164816
PCT Pub. Date: Oct. 29, 2015

(65) Prior Publication Data
US 2017/0056376 A1    Mar. 2, 2017

Related U.S. Application Data

(60) Provisional application No. 61/984,713, filed on Apr. 25, 2014.

(51) Int. Cl.
*A61K 31/423* (2006.01)
*A61K 31/404* (2006.01)
*A61K 31/428* (2006.01)

(52) U.S. Cl.
CPC .......... *A61K 31/423* (2013.01); *A61K 31/404* (2013.01); *A61K 31/428* (2013.01)

(58) Field of Classification Search
CPC ... A61K 31/404; A61K 31/423; A61K 31/428
USPC ....................................... 514/373
See application file for complete search history.

(56) References Cited

U.S. PATENT DOCUMENTS

| 4,594,348 A | | 6/1986 | Toja et al. |
| 6,150,531 A | * | 11/2000 | Lorenz ................. C07D 413/12 548/222 |
| 6,969,711 B2 | * | 11/2005 | Shibuya ............... C07D 235/28 514/218 |
| 9,893,301 B2 | * | 2/2018 | Park .................... H01L 51/0071 |
| 2014/0027741 A1 | * | 1/2014 | Park .................... H01L 51/0071 257/40 |
| 2017/0056376 A1 | * | 3/2017 | Wulff ................... A61K 31/423 |

OTHER PUBLICATIONS

Jenkins, David Paul et al., "Development of a QPatch Automated Electrophysiology Assay for Identifying KCa3.1 Inhibitors and Activators." Assay and Drug Development Technologies, 2013, vol. 11, No. 9/10, pp. 551-560.
Damkjaer, Mads et al. "Pharmacological activation of KCa3.1/KCa2.3 channels produces endothelial hyperpolarization and lowers blood pressure in conscious dogs." British Journal of Pharmacology, 2012, vol. 165, pp. 223-234.
Coleman, Nichole et al., "New Positive Ca2+-Activated K+ Channel Gating Modulators with Selectivity for KCa3.1." Molecular Pharmacology, Sep. 2014, vol. 86, pp. 342-357.
Mishra, Ramesh C. et al., "A pharmacologic activator of endothelial KCa channels enhances coronary flow in the hearts of type 2 diabetic rats." Journal of Molecular and Cellular Cardiology, Epub. Apr. 29, 2014, vol. 72, pp. 364-373.
PCT International Search Report dated Dec. 16, 2015 in related PCT Application No. PCT/US2015/027636.

* cited by examiner

*Primary Examiner* — Sabiha N Qazi
(74) *Attorney, Agent, or Firm* — Robert D. Buyan

(57) ABSTRACT

Benzoxazole and indole type KCa3.1 activators as well as the therapeutic uses of such compounds in human or animal subjects and their use in ex vivo preservation of organs or tissues.

18 Claims, 17 Drawing Sheets

SELECTIVE ACTIVATORS OF THE INTERMEDIATE CONDUCTANCE CA2+ACTIVATED K+ CHANNEL KCA3.1 AND THEIR METHODS OF USE

RELATED APPLICATIONS

This is the national stage filing under 35 U.S.C 371 of PCT International Patent Application No. PCT/US2015/027636 entitled Selective Activators of the Intermediate Conductance CA2+-Activated K+ Channel Kca3.1 and Their Methods of Use, filed Apr. 24, 2015, which claims the benefit of and right of priority to U.S. Provisional Patent Application No. 61/984,713 entitled Selective Activators Of The Intermediate Conductance Ca2+-Activated K+ Channel Kca3.1 And Their Methods Of Use filed on Apr. 25, 2014, the entirety of each such application being expressly incorporated herein by reference.

STATEMENT REGARDING GOVERNMENT SUPPORT

This invention was made with Government support under Grant No. NS072585, awarded by The National Institutes of Health. The Government has certain rights in this invention

STATEMENT REGARDING GOVERNMENT SUPPORT

This invention was made with United States Government support under Grant No. R21 NS072585 awarded by the National Institutes of Health. The United States Government may have certain rights in the invention.

FIELD OF THE INVENTION

The present invention relates generally to the fields of chemistry, pharmacology and medicine and more particularly to certain benzoxazole and indole type KCa3.1 activators as well as the therapeutic uses of such compounds in human or animal subjects and their use in ex vivo preservation of organs or tissues.

BACKGROUND OF THE INVENTION

Pursuant to 37 CFR 1.71(e), this patent document contains material which is subject to copyright protection and the owner of this patent document reserves all copyright rights whatsoever.

Abbreviations: In this patent application, the following abbreviations shall have the following meanings: AHP, afterhyperpolarization; BK, bradykinin; CaM, calmodulin; CamBD, calmodulin binding domain; CM-TMF, N-{7-[1-(4-chloro-2-methylphenoxy)ethyl]-[1,2,4]triazolo[1,5-a]pyrimidin-2-yl}-N'-methoxy-formamidine; CyPPA, cyclohexyl-[2-(3,5-dimethyl-pyrazole-1-yl-)6-methyl-pyrimidin-4-yl]-amine; DMSO, dimethyl sulfoxide; EBIO, 1-ethylbenzimidazolin-2-one; HEK, human embryonic kidney; HR, heart rate; KCa, $Ca^{2+}$-activated $K^+$ channel; KCa3.1, intermediate-conductance $Ca^{2+}$-activated $K^+$ channel; $K_V$, voltage-gated $K^+$ channel; MAP, mean arterial blood pressure; NS309, 6,7-dichloro-1H-indole-2,3-dione 3 oxime; PCA, porcine coronary arteries; PBS, phosphate buffered saline; SK, small-conductance KCa channel; SKA-31,naphtho[1,2-d]thiazol-2-ylamine; SKA-111, 5-methyl-naphtho[1,2-d]thiazol-2-amine; SKA-121, 5-methylnaphtho[2,1-d]oxazol-2-amine; TRAM-34, 1-[(2-chlorophenyl) diphenylmethyl]-1H-pyrazole; UCL1684,6,10-diaza-3(1,3) 8,(1,4)-dibenzena-1,5(1,4)-diquinolinacyclodecaphane; U46619, (Z)-7-[(1S,4R,5R,6S)-5-[(E,3S)-3-hydroxyoct-1-enyl]-3-oxabicyclo[2.2.1]heptan-6-yl]hept-5-enoic acid.

The human genome contains four voltage-independent $Ca^{2+}$ activated $K^+$ channels: the three small-conductance KCa2 channels, KCa2.1 (=KCNN1, SK1), KCa2.2 (=KCNN2, SK2) and KCa2.3 (=KCNN3, SK3), as well as the intermediate-conductance KCa3.1 (=KCNN4, IK1, SK4) (Joiner et al., 1997; Kohler et al., 1996; Wei et al., 2005). Their lack of voltage-dependence enables these channels to remain open at negative membrane potentials and to hyperpolarize the membrane towards values near the $K^+$ equilibrium potential of −89 mV. KCa3.1 and KCa2 channels are accordingly expressed in cells that need to be able to hyperpolarize in order to regulated $Ca^{2+}$ influx through inward rectifier $Ca^{2+}$ channels, pass on hyperpolarization through gap junctions or regulate firing frequency by preventing an untimely or premature action potential initiation (Adelman et al., 2012; Wulff and Köhler, 2013). Pharmacological activation of KCa channels has therefore been suggested for the treatment of various diseases. While KCa2 activators can potentially reduce neuronal excitability in CNS disorders like epilepsy and ataxia, KCa3.1 activators could be useful as endothelial targeted antihypertensives and to enhance fluid secretion in the airways in cystic fibrosis (Balut et al., 2012; Wulff et al., 2008; Wulff and Köhler, 2013).

All four KCa2/3 channels are voltage-independent and share a $Ca^{2+}$/calmodulin mediated gating mechanism (Fanger et al., 1999; Xia et al., 1998). Calmodulin (CaM), which can be regarded as a β-subunit for these channels, is constitutively bound to a calmodulin binding domain (CaMBD) in the intracellular C-terminus. Upon $Ca^{2+}$ binding to CaM the channels activate in a highly coordinated fashion with an extremely steep Hill-equation and $EC_{50}$ values in the range of 250 to 900 nM (Wei et al., 2005). KCa2/3 activators modulate this gating process and have therefore been termed "positive gating modulators". The oldest positive modulator of KCa2/3 channels is the benzimidazolone EBIO (Devor et al., 1996), which activates KCa3.1 with an $EC_{50}$ of ~30 μM and all three KCa2 channels with $EC_{50}$s around 300 μM (Wulff et al., 2013). Two structurally similar, but more potent molecules, are the oxime NS309 (Strobaek et al., 2004) and the benzothiazole SKA-31 (Sankaranarayanan et al., 2009). While NS309 is exquisitely potent (EC50 for KCa3.1 ~20 nM; $EC_{50}$ for KCa2 channels ~600 nM), it unfortunately has an extremely short in vivo half-live and inhibits KV11.1 (hERG) at a concentration of 1 μM (Strobaek et al., 2004). SKA-31 is 10-times less potent than NS309 but has become a relatively widely used in vivo tool compound to activate both KCa3.1 and/or KCa2 channels because of its long half-live of 12 h in rats (Sankaranarayanan et al., 2009). In contrast to these benzimidazole/benzothiazole-type KCa activators, which ail only show a very modest 5 to 10-fold selectivity for KCa3.1 and do not distinguish at all between the three KCa2 channels, CyPPA and its derivative NS13001 have a very different selectivity profile. Both compounds activate KCa2.3 and KCa2.2 but are completely inactive on KCa2.1 and KCa3.1 (Hougaard et al., 2007; Kasumu et al., 2012). GW542573X and (-)-CM-TMPF in contrast are selective for KCa2.1 (Hougaard et al., 2012; Hougaard et al., 2009). So while there are compounds that allow for the selective pharmacological activation of KCa2 channels, there currently is no selective KCa3.1 activator.

Intermediate-conductance KCa3.1 and small-conductance KCa2.3 channels are co-expressed in vascular endothelium, where they contribute to endothelium-derived hyperpolarization (EDH) vasodilator responses. Pharmacological activation of both channels has therefore been proposed as a novel endothelial function stimulating approach. However, while KCa3.1 channels are predominantly found in peripheral tissues, KCa2 channels are prominently expressed in neurons, where they underlie the medium afterhyperpolarization and regulate firing frequency. Application of higher concentrations of the currently available mixed KCa2/3 channel activators like SKA-31 therefore typically induce sedation and a reduction in heart rate that is presumably mediated through a central decrease of sympathetic drive.

Accordingly, there is a need in the art for the development of selective KCa3.1 activator(s) and methods for using such compounds for treatment of disease and for other applications.

SUMMARY OF THE INVENTIONS

In accordance with the present invention, certain examples and other aspects of the present invention are described below and in Appendixes A and B to this specification, as follows:

| Appendix | Description |
| --- | --- |
| A | Table showing chemical structures of claimed compounds |
| B | Table showing claimed derivatives of 5-methylnaphtho[1,2-d]oxazol-2-amine (SKA-120) and 5-methylnaphtho[2,1-d]oxazol-2-amine (SKA-121) |

In accordance with one aspect of the present invention, there are provided methods for treating hypertension, diabetic ischemia, or cystic fibrosis in a human or animal subject by administering to the subject a therapeutically active amount of a benzoxazole or indole compound which selectively activates KCa3.1 channels over KCa2 channels. In some embodiments, the benzoxazole or indole compound has approximately a 30-fold or greater selectivity, and more preferably approximately a 40-fold or greater selectivity, for KCa3.1 channels over KCa2 channels. Compounds useable in this method include but are not limited to 5-methylnaphtho[1,2-d]oxazol-2-amine (SKA-120) and 5-methylnaphtho[2,1-d]oxazol-2-amine (SKA-121) as well as the other compounds listed in Appendixes B and C.

In accordance with another aspect of the present invention, there are provided methods for preserving the function of the vascular endothelium of an organ or tissue that has been removed from the body of a human or animal subject, such methods comprising the step of contacting the organ or tissue with a benzoxazole and indole compound as described herein. The organ or tissue may be immersed in or perfused with a solution with contains a compound of the present invention.

Still further aspects and details of the present invention will be understood upon reading of the detailed description and examples set forth herebelow.

BRIEF DESCRIPTION OF THE DRAWINGS

The following figures are included in this patent application and referenced in the following Detailed Description and Examples:

FIG. 4A shows exemplary traces of $K_{Ca}3.1$ and $K_{Ca}2.3$ activation by SKA-111 and concentration-response curves for $K_{Ca}3.1$ ($EC_{50}$ 111±27 nM, $n_H$ 1.5), $K_{Ca}2.3$ ($EC_{50}$ 13.7±6.9 µM, $n_H$ 1.9), $K_{Ca}2.1$ ($EC_{50}$ 8.1±0.4 µM, $n_H$ 4.5) and $K_{Ca}2.2$ ($EC_{50}$ 7.7±1.9 µM, $n_H$ 2.3). FIG. 4B shows exemplary traces of $K_{Ca}3.1$ and $K_{Ca}2.3$ activation by SKA-121 and concentration-response curves for $K_{Ca}3.1$ ($EC_{50}$ 109±14 nM, $n_H$ 3.0), $K_{Ca}2.3$ ($EC_{50}$ 4.4±2.3 µM, $n_H$ 1.6), $K_{Ca}2.1$ ($EC_{50}$ 8.7±1.6 □M, $n_H$ 4.1) and $K_{Ca}2.2$ ($EC_{50}$ 6.8±2.2 µM, $n_H$ 1.7). All data points are means±SD. FIG. 4C shows representative currents from inside-out patches in the presence of 0.3 µM (top) and 1 µM (bottom) $Ca^{2+}$ before and after application of 1 µM SKA-121. FIG. 4D shows $K_{Ca}3.1$ current at −75 mV in an inside-out patch exposed to varying $Ca^{2+}$ concentrations as a function of time. (Note: SKA-121 applied with 500 nM $Ca^{2+}$ was washed out with 1 µM $Ca^{2+}$). FIG. 4E shows the $Ca^{2+}$ concentration—response curve for $K_{Ca}3.1$ activation measured from inside out patches in absence or presence of 1 µM SKA-121. Currents from individual patches were normalized to the effect of 10 µM $Ca^{2+}$ in the absence of SKA-121. Data are mean±SD (n=3 per data point). F, Blockade of $K_{Ca}3.1$ and $K_{Ca}2.3$ currents activated by SKA-121 by TRAM-34 and UCL1684.

FIG. 6A shows that intraperitoneal injections of SKA-111 (panels on left) and SKA-121 (panels on right) reduced mean arterial blood pressure (MAP) in wild-type mice. SKA-111 (on left) but not SKA-121 (on right) severely reduced heart rate (HR). As indicated by the dashed line (right panel), SKA-111-treated animals were initially handled and warmed to avoid fatal hypothermia during strong bradycardia. Ve=Vehicle control. Black and white marked intervals of x-axis indicate dark and light periods. FIG. 6B shows that SKA-121 (on right) and, to a lesser extent, SKA-111 (on left) reduced blood pressure in L-NAME-treated moderately hypertensive mice. Heart rate remained virtually stable. FIG.

6C shows cardiovascular effects of SKA-111 and SKA-121 in KCa3.1$^{-/-}$ mice. At a dose of 100 mg/kg, SKA-111 reduced MAP and HR but SKA-121 did not. SKA-111 also reduced HR at a dose of 30 mg/kg. Data points are means±SEM; n=3-4 experiments per strain and compound. Lines indicate time periods when pressures or heart rates were significantly different from Ve. *<0.05, unpaired Student T-test.

Figure 7A:
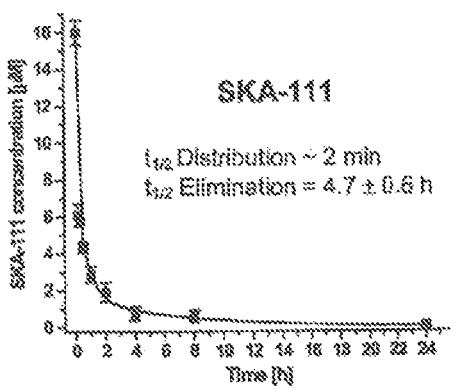
Figure 7B:
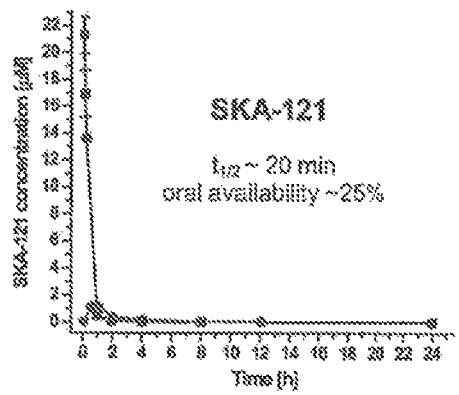
Figure 7C:
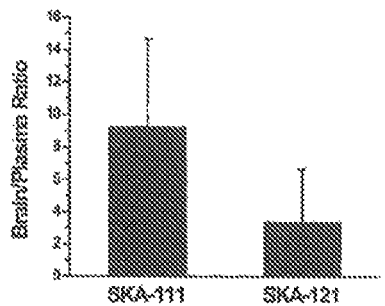

FIGS. 7A-7C are graphs which show pharmacokinetics of SKA-111 and SKA-121. FIG. 7A shows total SKA-111 plasma concentration (mean±S.D.) versus time after intravenous administration of 10 mg/kg to mice (n=2-3 per time point). FIG. 7B shows total SKA-121 plasma concentrations (mean±S.D.) versus time following intravenous (black) and oral (red) application of 10 mg/kg to mice (n=3 per time point). FIG. 7C shows brain/plasma concentration ratios for SKA-111 and SKA-121 determined from multiple paired brain and plasma samples obtained during the experiments shown in A and B (n=8 for SKA-111 and n=5 for SKA-121).

Figure 8A:
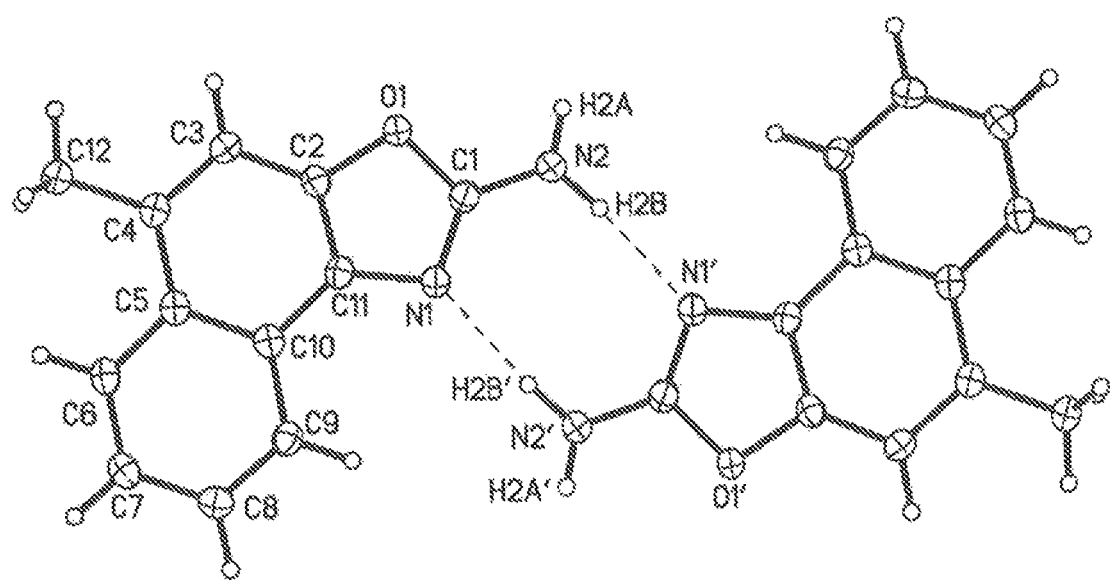
Figure 8B:
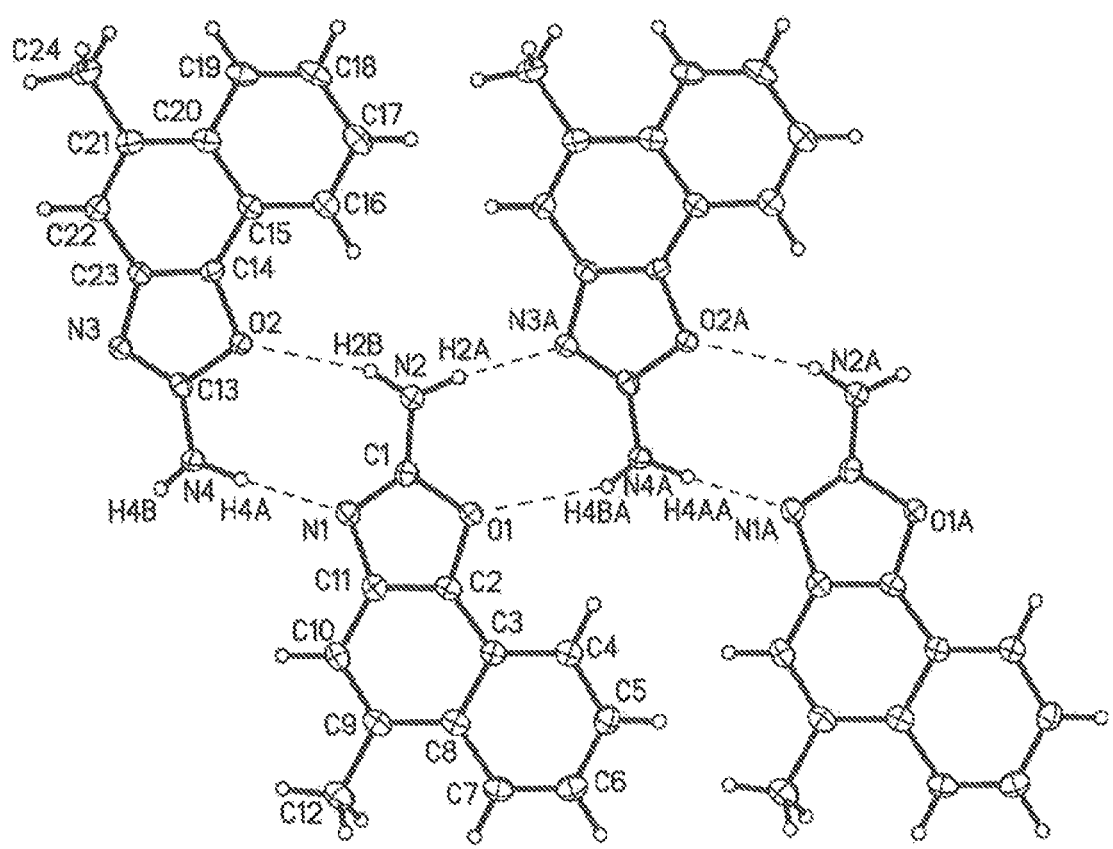

FIGS. 8A and 8B show differences in the hydrogen bonding pattern in the crystal structures of SKA-120 and SKA-121. FIG. 8A is a diagram of the hydrogen bonding scheme for SKA-120 and FIG. 8B is a diagram of the hydrogen bonding scheme for SKA-121.

Figure 9A:
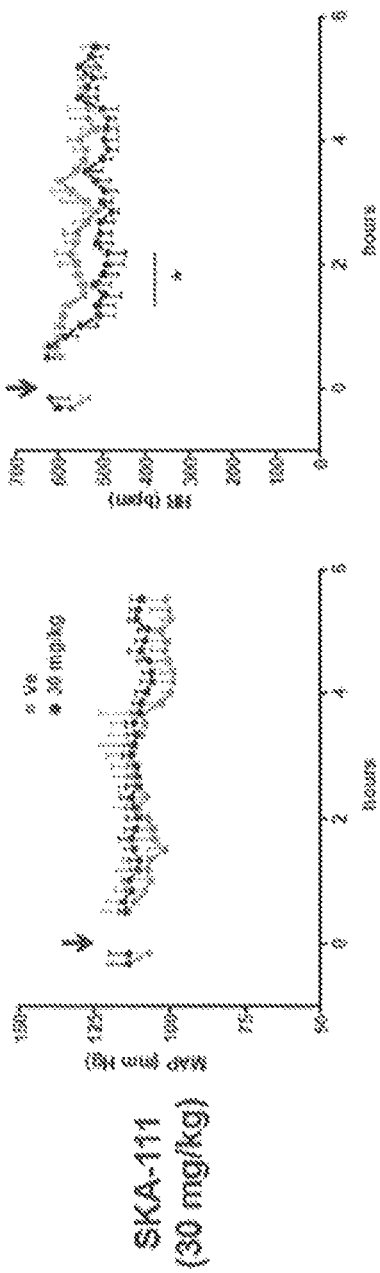
Figure 9B:
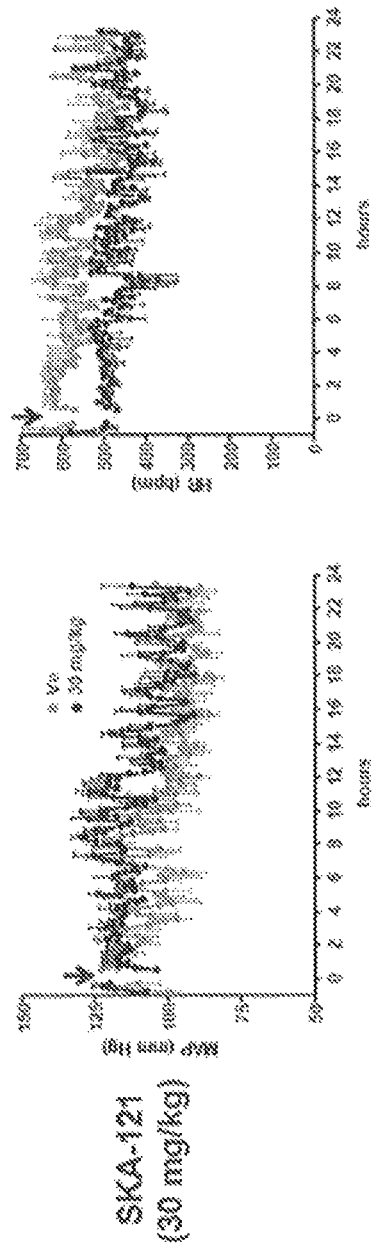

FIGS. 9A and 9B show telemetric mean arterial blood pressure (MAP) measurements after i.p. injection of either 30 mg/kg SKA-111, 30 mg/kg SKA-121 or vehicle (Ve). FIG. 9A shows data for SKA-111 and Ve. FIG. 9B shows data for SKA-121 and Ve. SKA-111 moderately reduced heart rate (HR) at 2 h after injection. Neither SKA-111 nor SKA-121 caused significant changes in mean arterial blood pressure (MAP). Data points are means±SEM; n=3-4 per group. Horizontal line with asteric (*) shown on right panel of FIG. 9A indicates time period when HR of SKA-121 treated animals was was significantly different from that of Ve treated animals (p<0.05, unpaired Student T-test).

DETAILED DESCRIPTION OF THE INVENTION

The following detailed description and the accompanying drawings to which it refers are intended to describe some, but not necessarily all, examples or embodiments of the invention. The described embodiments are to be considered in all respects only as illustrative and not restrictive. The contents of this detailed description and the accompanying drawings do not limit the scope of the invention in any way.

Applicants had previously used riluzole, a drug for the treatment of amyotrophic lateral sclerosis, as a template for the design of SKA-31. Riluzole is a "dirty" compound, which exerts multiple pharmacological activities, the most prominent of which are inhibition of voltage-gated sodium (Na$_V$) channels at concentrations of 1-50 μM (Debono et al., 1993; Duprat et al., 2000) and activation of K$_{Ca}$2/3 channels with EC$_{50}$s of 10-20 μM (Grunnet et al., 2001). Through directed derivatization of riluzole applicants managed to significantly reduce Na$_V$ channel blocking effects and increase activity on K$_{Ca}$2/3 channels. While SKA-31 only affects Na$_V$ channels at concentrations of 25 μM or higher, it activates K$_{Ca}$2.3 with an EC$_{50}$ of 3 μM and K$_{Ca}$3.1 with an EC$_{50}$ of 260 nM. Since both K$_{Ca}$3.1 and K$_{Ca}$2.3 are expressed in vascular endothelium and have been shown to be involved in the so called endothelium-derived hyperpolarization (EDH) response (Dalsgaard et al., 2010; Edwards et al., 2010; Grgic et al., 2009; Köhler et al., 2010), SKA-31 was used as a pharmacological tool to explore the role of K$_{Ca}$ channels in blood-pressure regulation. While mice deficient in K$_{Ca}$3.1 and/or K$_{Ca}$2.3 exhibit impaired EDH responses and an increased mean arterial blood pressure (Brahler et al., 2009), pharmacological K$_{Ca}$ channel activation with SKA-31 was found to lower blood pressure in both mice and dogs (Damkjaer et al., 2012; Radtke et al., 2013; Sankaranarayanan et al., 2009). In dogs intravenous injection of 2 mg/kg SKA-31 produced an immediate and strong (−30 mmHg), but short-lived reduction in blood pressure (Damkjaer et al., 2012). In mice, SKA-31 doses of 10-30 mg/kg have been reported to lower blood pressure more prolonged (~30 mmHg for 60-90 min) (Köhler, 2012; Sankaranarayanan et al., 2009). Significant blood pressure lowering effects with SKA-31 doses of 30 mg/kg have been further observed in models of hypertension like angiotensin-II infused (Sankaranarayanan et al., 2009) and connexin 40-deficient mice (Radtke et al., 2013), which exhibit severe chronic renin-dependent hypertension. However, the responses typically lasted only about 1 h. Higher doses of SKA-31 (100 mg/kg) induced a stronger and longer-lasting response, which was accompanied by significant bradycardia. This reduction in heart rate was probably due to a centrally mediated decrease in sympathetic drive through activation of neuronal K$_{Ca}$2 channels by the brain penetrant SKA-31 as well as possible direct effects on K$_{Ca}$2 channels in cardiac pacemaker tissue (Radtke et al., 2013). Another side-effect that might prohibit the use of K$_{Ca}$2 activators as antihypertensives is a possible impairment of learning and memory because of the role neuronal K$_{Ca}$2 channels play in in synaptic plasticity and long-term potentiation (Adelman et al., 2012; Blank et al., 2003). In order to avoid these K$_{Ca}$2 channel mediated side effects it therefore seems highly desirable to identify selective K$_{Ca}$3.1 activators which could be used as pharmacological tools to further dissect the in vivo role of K$_{Ca}$3.1 in blood pressure control and to help determine whether K$_{Ca}$3.1 activators could eventually be developed into a new class of endothelial targeted antihypertensives. Applicants therefore modified the benzothiazole SKA-31 and developed a K$_{Ca}$3.1 selective small molecule activator—SKA-121. SKA-121, a compound generated through an isosteric replacement approach, activates K$_{Ca}$3.1 with an EC$_{50}$ of 111 nM, exhibits 40-80-fold selectivity over the three K$_{Ca}$2 channels and lowers blood pressure in mice as determined by telemetry without exerting K$_{Ca}$2 channel mediated effects on heart rate.

Material and Methods

Commercially Available Compounds. 2-Amino-4-(1-naphthyl)thiazole (SKA-75, CAS# 56503-96-9), 2-amino-4-(2-naphthyl)thiazole (SKA-76), CAS# 21331-43-1), 2,3,3-trimethyl-3H-benzo[g]indole (SKA-92, CAS. 74470-85-2), 2-methylnaphtho[2,3-d]oxazole (SKA-104, CAS# 20686-66-2), and 2-methylnaphtho[2,1-d]oxazole (SKA-103, CAS# 85-15-4) were purchased from Alfa Aesar (Pelham, N.H.); 2-methylnaphtho[1,2-d]thiazole (SKA-74, 2682-45-3) was purchased from Sigma (St. Louis, Mo.).

Chemical Synthesis. Compounds that were not commercially available were synthesized in our laboratory by the general methods described below. Compounds reported previously were characterized by melting point, $^1$H NMR and $^{13}$C NMR to confirm their chemical identity. New chemical entities (NCEs) were additionally characterized by high resolution mass spectrometry (HRMS) and a fully interpreted $^{13}$C NMR.

General Method I. Preparation of Thiazoles. Thiourea (17 mmol) was added to a solution of substituted ketones (6 mmol) in 30 mL absolute ethanol. The mixture was refluxed for 8 h, which resulted in 2-aminothiazole hydrobromide salts. The 2-aminothiazole was obtained by treating the hydrobromide salt with 2M NaOH (5 ml) and extracting with ethyl acetate. The crude residue was concentrated, reconstituted in a methanol-water mixture (99:1), treated with charcoal and re-crystallized.

General Method II. Alternative Prepartion Of Benzothiazoles. Thiourea (17 mmol) was added to a solution of substituted ketones (6 mmol) in 30 ml absolute ethanol. The mixture was refluxed for 8 h, which resulted in 2-aminothiazole hydrobromide salts. The free 2-aminothiazole was obtained by treating the hydrobromide salt with 2M NaOH (5 ml) and extracting with ethyl acetate. The crude residue was concentrated, reconstituted in a methanol-water mixture (99:1), treated with charcoal and re-crystallized. The resulting 2-aminothiazole, 2-iodoxybenzoic acid (IBX) and tetrabutyl ammonium tribromide (TBAB) were combined in ethyl acetate and stirred at room temperature (RT) for 10 h. The reaction mixture was filtered through a pad of celite, the filtrate was diluted with saturated $Na_2S_2O_3$ and extracted with ethyl acetate. The combined organic layers were dried with anhydrous sodium sulfate (anhydrous $Na_2SO_4$), concentrated, and then purified via flash chromatography (cyclohexane-EtOAc, 1:1).

General Method III. Preparation of Benzothiazoles. Benzoyl chloride was added drop wise to a stirred solution of $NH_4SCN$ in acetone and stirred at 50° C. for 2 h. Next, a solution of substituted naphthylamines in acetone was added drop wise and the mixture was stirred at 50° C. for 24 h. The reaction mixture was diluted with water, the precipitated crystals collected by filtration, and washed with water. The crystals were then suspended in 2M NaOH (50 ml), refluxed for 1 h and poured into cold water and filtered. The crude crystals of the resulting thiourea were dissolved in acetic acid to which benzyl trimethyl ammonium tribromide was added and allowed to react overnight. Ethyl ether ($Et_2O$) was added and the precipitate of the resulting product-HBr salt was collected by filtration and washed with $Et_2O$. The salt was then treated with 1M NaOH to liberate the free base which was recrystallized in methanol.

General Method IV: Preparation of 2-Aminonaphthooxazoles. To procure the intermediate 2-hydroxy-naphthalenones substituted ketones (1 g, 6.2 mmol) were added to a stirred mix of water (25 ml), acetonitrile (25 ml) trifluoroactic acid (6 ml, 7 mmol), iodobenzene (0.7 ml, 6 mmol) and oxone (11 g, 37 mmol). The resulting solution was refluxed for 1 hand the progress of the reaction was monitored by TLC. The reaction was then allowed to cool to RT and filtered. The mixture was extracted with ethyl acetate (3×30 ml) and lastly neutralized with saturated $NaHCO_3$ (3×30 ml). The combined organic phase was washed with brine (30 ml), dried with anhydrous $Na_2SO_4$, filtered and concentrated. The residue was purified by flash chromatography over silica gel (cyclohexane-EtOAc, 3:1) to give substituted 2-hydroxy-naphthalenones ($R_f$=0.20). The preparation of 2-aminonaphthooxazole began by adding cyanamide (2 mmol) to a stirred solution of substituted 2-hydroxy-naphthalenone (1.5 mmol), wafer (20 ml), and acetonitrile (10 ml). The resulting mixture was refluxed for 15 h and the progression of the reaction was monitored by TLC. The reaction was allowed to cool to RT. The mixture was extracted with ethyl acetate (3×30 ml) to give a mixture of isomers. The combined organic phase was washed with brine (30 ml), dried with anhydrous $Na_2SO_4$, filtered and concentrated. The isomers were purified and separated by flash chromatography over silica gel, (cyclohexane-EtOAc, 1:1).

8H-Indeno[1,2-d]thiazol-2-amine (SKA-69). SKA-69 was prepared from 1-indanone (1 g, 4.7 mmol) according to general method I. The product was isolated as brown crystals (563 mg, 63%); m.p.=212° C. (CAS. 85787-95-7). $^1$H NMR (500 MHz, DMSO-$d_6$, δ): 7.45 (d, J=7.4 Hz, 1H, 4-H), 7.37 (d, J=7.4 Hz, 1H, 7-H), 7.28 (t, J=7.4 Hz, 1H, 5-H), 7.17–7.11 (m, 3H, 6-H and $NH_2$), 3.68 (s, 2H, $CH_2$). $^{13}$C NMR (125 MHz: DMSO-$d_6$, δ):173.74, 146.09, 138.04, 128.58, 126.68, 126.60, 125.47, 118.2, 32.85.

4,5-Dihydronaphtho[1,2-d]thiazol-2-amine (SKA-70). SKA-70 was prepared from 1-tetralone (1 g, 6.84 mmol) according to general method I. The product was isolated as white crystals (906 mg, 64%); m.p.=135° C. (CAS. 34176-49-3). $^1$H NMR (500 MHz, DMSO-$d_6$, δ): 7.52 (d, J=7.3 Hz, 1H, 9-H), 7.23–7.14 (m, 2H, 7-H and 6-H), 7.10 (t, J=7.3 Hz, 1H, 8-H), 6.93 (s, 2H, $NH_2$), 2.93 (t, J=7.8 Hz, 2H, 5-H), 2.76 (t, J=7.8 Hz, 2H, 4-H). $^{13}$C NMR (125 MHz: DMSO-$d_6$, δ): 167.28, 145.01, 134.99, 132.39, 128.37, 127.31, 126.87, 122.83, 118.25, 29.18, 21.79.

6-Fluoro-8H-indeno[1,2-d]thiazol-2-amine(SKA-71). SKA-71 was prepared from 5-fluoro-1-indanone (1.84 g, 12.4 mmol) according to general method I. The product was isolated as lavender crystals (934 mg, 40%); m.p.=217° C. dec (CAS. 1025800-52-5). $^1$H NMR (500 MHz, DMSO-$d_6$, δ): 7.33 (dt, J=7.9, 3.8 Hz, 2H, 4-H, and 7-H), 7.16 (s, 2H, $NH_2$), 7.10 (ddd, J=10.2, 8.4, 2.5 Hz, 1H, 5-H), 3.70 (s, 2H, $CH_2$). $^{13}$C NMR (125 MHz: DMSO-$d_6$, δ): 182.98, 160.95, 139.84, 128.3, 126.68, 126.53, 124.01, 114.03, 112.77, 32.72.

5-Chloronaphtho[1,2-d]thiazol-2-amine (SKA-72). SKA-72 was prepared from 1-amino-4-chloronaphthalene (1.6 g, 8.8 mmol) according to general method III. The product was isolated as lavender crystals (1.27 g, 60%); m.p.=253° C. (CAS. 1369250-74-7). $^1$H NMR (500 MHz, DMSO-$d_6$, δ): 8.41 (m, 1H, 9-H), 8.14 (m, 1H, 6-H), 8.07 (s, 1H, 4-H), 7.75 (s, 2H, $NH_2$), 7.63 (m, 2H, 8-H and 7-H). $^{13}$C NMR (125 MHz: DMSO-$d_6$, δ): 168.17, 147.65, 128.19, 126.46, 126.40, 126.22, 124.82, 124.14, 123.94, 122.07, 119.66.

4,5-Dihydroaceoaphtho[5,4-d]thiazol-8-amine (SKA-73). SKA-73 was prepared from 1,2-dihydroacenaphthylen-5-amine (0.4 g, 2 mmol) according to general method III. The product was isolated a brown solid (400 mg, 30%); m.p.=257° C. (CAS. 108954-84-3). $^1$H NMR (500 MHz, DMSO-$d_6$, δ): 7.87 (d, J=8.2 Hz, 1H, 9-H), 7.56 (s, 1H, 4-H), 7.45 (t, J=7.5 Hz, 1H, 8-H), 7.30–7.20 (m, 3H, 7-H and $NH_2$), 3.37 (d, J=12.2 Hz, 4H, 4-H and 5-H). $^{13}$C NMR (125 MHz: DMSO-$d_6$, δ): 167.17, 146.65, 139.05, 128.19, 128.46, 124.40, 119.66, 119,24, 113.08, 31.25, 29.92. Note: We are following the NMR numbering designation of 2-aminobenzothiazoles and not dihydroacenaphthothiazoles.

7,8-Dihydro-6H-indeno[4,5-d]thiazol-2-amine (SKA-81). SKA-81 was prepared from 4-aminoindan (500 mg, 3.7 mmol) according to general method III. The product was isolated as a white solid (200 mg, 30%); m.p.=195° C. $^1$H NMR (500 MHz, DMSO-$d_6$, δ): 7.38–7.37 (d, J=7.75 Hz, 1H, 5-H), 7.25 (s, 2H, $NH_2$), 6.90 (d, J=7.8 Hz, 1H, 4-H ), 3.00 (t, J=7.3, 2H, 8-H), 2.91 (t, J=7.3 Hz, 2H, 6-H), 2.10–2.04 (q, J=7.3 Hz, 2H, 7-H). $^{13}$C NMR (125 MHz, DMSO-$d_6$, δ): 167.37 (2-C), 149.90 (3-C), 141.97 (4-C), 133.02 (6-C), 129.00 (8-C), 119.08 (5-C), 117.58 (4-C), 33.42 (6-C), 31.55 (8-C), 25.62 (7-C). HRMS (ESI): calcd: 191.0637; found: 191.0638.

5-Bromooaphtho[1,2-d]thiazol-2-amine (SKA-S87). SKA-87 was prepared from 1-amino-4-bromonaphthalene (1.6 g, 8.8 mmol) according to general method III. The product was isolated as silver crystalline rods (500 mg, 45%); m.p.=253° C. (CAS. 412312-09-5). $^1$H NMR (800

MHz, DMSO-d$_6$, δ): 8.40 (d, J=8.6 Hz, 1H, 9-H), 8.24 (s, 1H, 4-H), 8.10 (d, J=8.1 Hz, 1H, 6-H), 7.78 (s, 2H, NH$_2$), 7.65–7.60 (m, 2H, 7-H and 6-H). $^{13}$C NMR (125 MHz, DMSO-d$_6$, δ): 168.67, 148.68, 129.71, 127.10, 127.00, 126.89, 126.88, 125.90, 124.61, 123.50, 112.73.

Naphtho[1,2-d]oxazol-2-amine (SKA-102). Solid 1-amino-2-naphthol hydrochloride (0.80 g, 4 mmol) was suspended in 20 ml dichloromethane (DCM), treated with triethylamine (0.6 ml, 20 mmol) and cyanogen bromide (3M BrCN in DCM; 3 ml, 6.2 mmol), and allowed to react overnight yielding naphtho[1,2-d]oxazol-2-amine HBr. To isolate the free amine, the HBr salt was suspended in ethyl acetate and free based with ammonium hydroxide (NH$_4$OH). The solid residue was dissolved in a diethyl ether-ethyl acetate, treated with charcoal and re-crystallized from diethyl ether-ethyl acetate (10:1), resulting in a purple solid (100 mg, 45%); m.p.=194° C. (CAS. 858432-45-8). $^1$H NMR (800 MHz, DMSO-d$_6$, δ): 8.27 (d, J=8.3 Hz, 1H, 9-H), 7.9 (d, 1H, J=8.16 Hz, 6-H ), 7.60 (d, J=8.88 Hz, 1H, 5-H), 7.58 (t, J=7.92 Hz, 1H, 8-H), 7.53 (d, J=8.72 Hz, 1H, 4-H), 7.47 (t, J=8.01 Hz, 1H, 8-H). $^{13}$C NMR (200 MHz, DMSO-d$_6$, δ): 163.25, 144.14, 138.53, 130.95, 128.80, 125.97, 124.72, 124.49, 121.99, 120.29, 110.32.

5-Fluoronaphtho[1,2-d]thiazol-2-amme (SKA-106). SKA-106 was prepared from 4-fluoronaphthalen-1-amine (1 g, 6 mmol) according to general method III. The product was isolated as a clear oil (210 mg, 20%). $^1$H NMR (500 MHz, acetone-d$_6$, δ): 8.48 (d, J=8.1 Hz, 1H, 9-H), 8.06 (d, J=8.2 Hz, 1H, 6-H), 7.62 (m, 3H, 8-H, 7-H and 4-H), 6.91 (s, 2H, NH$_2$). $^{13}$C NMR (125 MHz, acetone-d$_6$, δ): 167.23 (2-C), 157.95 (5-C), 145.12 (3'-C), 128.33 (6-C), 125.17 (1'-C), 126.94 (7-C), 125.80 (9-C), 125.01 (8-C) 124.29 (9'-H), 116.06 (6'-C), 103.59 (4-C). HRMS (ESS): calcd: 219.0387; found: 219.0383.

2-Aminonaphtho[1,2-d]thiazole-5-carbonitrile (SKA-107). SKA-107 was prepared from 4-amino-1-naphthalen-ecarbonitrile (1 g, 6 mmol) according to general method III. The product was isolated as a brown solid (121 mg, 45%); m.p.=265° C. $^1$H NMR (500 MHz, acetone-d$_6$, δ): 8.62 (d, J=8.22 Hz, 1H, 9-H), 8.42 (s, 1H, 4-H), 8.20 (d, J=8.34 Hz, 1H, 6-H), 7.78 (t, J=7.04 Hz, 1H, 7-H), 7.73 (t, J=7.25 Hz, 1H, 8-H), 7.48 (s, 2H, NH$_2$). $^{13}$C NMR (200 MHz, DMSO-d$_6$, δ): 171.82 (2-C), 153.14 (3'-C), 131.15 (6-C), 128.32 (4-C), 127.55 (9-C), 127.39 (8-C), 125.25 (7-C), 124.96 (6'-C), 124.84 (1'-C), 124.69 (9'-C), 118.94 (CN), 99.96 (5-C). HRMS (ESI): calcd: 226.0433; found: 226.0432.

6,8-Dimethyl-4,5-dihydronaphtho[1,2-d]thiazol-2-amine (SKA-108). SKA-108 was prepared from 5,7-dimethyl-1-tetralone (2 g, 11 mmol) according to general method I. The product was isolated as pink crystals (300 mg, 16%); m.p.=159° C. $^1$H NMR (500 MHz, acetone-d$_6$, δ): 7.40 (s, 1H, 9-H), 6.83 (s, 1H, 7-H), 6.17 (s, 2H, NH$_2$), 2.91 (t, J=7.87 Hz, 2H, 4-H), 2.81 (t, J=7.56 Hz, 2H, 5-H), 2.27 (s, 3H, 8-CH$_3$), 2.25 (s, 3H, 6-CH$_3$). $^{13}$C NMR (200 MHz, DMSO-d$_6$, δ): 166.86 (2-C), 145.13 (3'-C), 135.11 (8-C), 135.09 (6-C), 131.86 (6'-C), 129.81 (7-H), 129.41 (9'-C), 121.69 (9-C), 117.36 (1'-C), 28.8 (4-CH$_2$), 24.57 (5-CH$_2$), 21.37 (8-CH$_3$), 19.88 (6-CH$_3$). HRMS (ESI): calcd: 231.0950; found: 231.0949.

6,8-Dimethylnaphtho[1,2-d]thiazol-2-amine (SKA-109). SKA-109 was prepared from 5,7-dimethy-1-tetralone (2 g, 11 mmol) according to general method II. The product was isolated as pink crystals (15 mg, 0.6%); m.p.=157° C. $^1$H NMR (500 MHz, DMSO-d$_6$, δ): 8.02 (s, 1H, 9-H), 7.73 (d, J=8.81 Hz, 1H, 4-H), 7.59 (d, J=8.84 Hz, 1H, 5-H), 7.53 (s, 2H, NH$_2$), 7.17 (s, 1H, 7-H), 2.61 (s, 3H, 8-CH$_3$), 2.45 (s, 3H, 6-CH$_3$). $^{13}$C NMR (125 MHz, DMSO-d$_6$, δ): 167.84 (2-C), 148.80 (3'-C), 135.61 (8-C), 134.92 (6-C), 128.70 (7-C), 126.90 (9-C), 121.68 (6'-C), 118.78 (1'-C), 117.57 (4-C), 100.61 (9-C), 99.85 (5-C), 22.21 (8-CH$_3$), 20.14 (6-CH$_3$). HRMS (ESI): calcd: 222.0794; found: 222.0794.

Thieno[2',3':5,6]benzo[1,2-d]thiazol-2-amine (SKA-110). SKA-110 was prepared from 6,7-dihydro-4-benzo[b] thiophenone (0.5 g, 3 mmol) according to general procedure II. The product was isolated as a white solid (26 mg, 3.8%), m.p.=161° C. (CAS. 35711-03-6). $^1$H NMR (800 MHz, DMSO-d$_6$, δ): 7.71 (d, J=5.36 Hz, 1H, 7-H), 7.68–7.62 (m, 4H, 4-H, 5-H, and NH$_2$), 7.58 (d, J=5.41 Hz, 1H, 6-H). $^{13}$C NMR (125 MHz, DMSO-d$_6$, δ): 168.26, 147.81, 137.83, 131.22, 126.97, 125.72, 121.95, 117.97, 115.51.

5-Methylnaphtho[1,2d]thiazol-2-amine (SKA-111). SKA-111 was prepared from 4-methyl-1-tetralone (1 g, 11 mmol) according to general procedure II. The product was isolated as yellow crystals (100 mg, 16%); m.p.=209° C. (CAS. 1369170-24-0). $^1$H NMR (800 MHz, DMSO-d$_6$, δ): 8.96 (d, J=7.86 Hz, 1H, 9-H), 8.46 (d, J=7.99 Hz, 1H, 6-H), 8.06 (s, 1H, 4-H), 7.98 (dt, J=6.83, 13.83 Hz, 2H, 7-H and 8-H), 7.16 (s, 2H, NH$_2$), 3.14 (s, 3H, CH$_3$). $^{13}$C NMR (125 MHz, DMSO-d$_6$, δ): 166.73, 147.60, 131.54, 127.88, 127.33, 126.02, 125.58, 125.27, 124.75, 124.70, 119.39, 19.01.

8-Fluoronaphtho[1,2-d]thiazol-2-amine (SKA-112). SKA-112 was prepared from 7-fluoro-1-tetralone (0.5 g, 3 mmol) according to general procedure II. The product was isolated a clear oil (10 mg, 3%). $^1$H NMR (500 MHz, DMSO-d$_6$, δ): 8.00 (dd, J=5.74, 9.02 Hz, 1H, 7-H), 7.90 (dd, J=2.67, 10.46 Hz, 1H, 9-H ), 7.79 (d, J=8.61 Hz, 1H, 5-H), 7.67 (s, 2H, NH$_2$), 7.60 (d, J=8.64 Hz, 1H, 4-H), 7.37 (td, J=2.73, 8.83 Hz, 1H, 6-H). $^{13}$C NMR (125 MHz, DMSO, δ): 168.40 (2-C), 161.60 (8-CF), 159.67 (3'-C), 148.183 (6-C), 131.73 (6'-C), 129.52 (1'-C), 126.84 (9'-C), 121.27 (7-C), 119.43 (4-C), 115.54 (5-C), 107.29 (9-C). HRMS (ESI): calcd: 219.0387; found: 219.0383.

5-Methyl-4,5-dihydronaphtho[1,2-d]thiazol-2-amine (SKA-113). SKA-113 was prepared from 4-methyl-1-tetralone (2 g, 11 mmol) according to general procedure I. The product was isolated as white crystals (250 mg, 20%); m.p.=109° C. dec (CAS. 896156-31-3). $^1$H NMR (500 MHz, DMSO-d$_6$, δ): 7.56 (d, J=6.4 Hz, 1H, 9-H), 7.40 (s, 2H, NH$_2$), 7.21 (m, 3H, 6-H, 7-H and 8-H), 3.12 (h, J=6.8 Hz, 1H, 5-H), 2.76 (ddd, J=175.4, 16.2, 6.6 Hz, 2H, 4-CH$_2$), 1.23 (d, J=6.9 Hz, 3H, 5-CH$_3$). $^{13}$C NMR (125 MHz, DMSO-d$_6$, δ): 167.85, 152.42, 140.02, 127.69, 127.37, 127.29, 122.97, 116.67, 99.85, 33.48, 29.20, 21.45.

6-Methoxy-4,5-dihydronaphtho[1,2-d]thiazol-2-amine (SKA-114). SKA-114 was prepared from 5-methoxy-1-tetralone (2 g, 11 mmol) according to general procedure I. The product was isolated as brown crystals (1.5 g 57%); m.p.=200° C. (CAS. 489430-53-7). $^1$H NMR (500 MHz, DMSO-d$_6$, δ): 7.23–7.13 (m, 2H, 9-H and 8-H), 6.91 (s, 2H, NH$_2$), 6.84 (d, J=7.59 Hz, 1H, 7-H), 3.79 (s, 3H, OCH$_3$), 2.89 (t, J=8.09 Hz, 2H, 4-CH$_2$), 2.73 (t, J=8.07 Hz, 2H, 5-CH$_2$). $^{13}$C NMR (125 MHz, DMSO-d$_6$, δ): 167.04, 156.69, 144.90, 133.25, 127.75, 122.02, 118.20, 115.94, 110.01, 56.10, 21.50, 21.18.

5-Methoxynaphtho[1,2-d]thiazol-2-amine (SKA-117). SKA-117 was prepared from 1-amino-4-methoxynaphthalene (0.1 g, 0.51 mmol) according to general method III. The product was isolated as lavender crystals (16 mg, 14%); m.p.=213° C. (CAS. 1368289-59-1). $^1$H NMR (500 MHz, DMSO-d$_6$, δ); 8.87 (d, J=8.25 Hz, 1H, 9-H), 8.68 (d, J=8.3 Hz, 1H, 6-H), 8.02 (t, J=7.4 Hz, 1H, 7-H), 7.95 (t, J=7.4 Hz, 1H, 8-H), 7.56 (s, 1H, 4-H), 7.11 (s, 2H, NH$_2$), 4.49 (s, 3H, OCH$_3$). $^{13}$C NMR (125 MHz, DMSO-d$_6$, δ: 168.11, 155.81, 148.63, 127.48, 126.6, 126.56, 123.94, 119.16, 116.51, 114.98, 104.55, 56.26.

5-Methylnaphtho[1,2-d]oxazol-2-amine (SKA-120). SKA-120 was prepared from 4-methyl-1-tetralone according to general procedure IV. The product was isolated as light brown crystals (50 mg, 4%); m.p.=209° C.; R$_f$=0.38 (cyclohexane-EtOAc, 1:1). $^1$H NMR (800 MHz, CDCl$_3$, δ): 8.28 (d, J=8.3 Hz, 1H, 9-H), 8.03 (d, J=8.4 Hz, 1H, 6-H), 7.58 (t, J=7.4 Hz, 1H, 8-H), 7.52 (t, J=7.5 Hz, 1H, 7-H), 7.38 (s, 1H, 4-H), 5.39 (bs, 2H, NH$_2$), 2.74 (s, 3H, CH$_3$). $^{13}$C NMR (200 MHz, CDCl$_3$, δ): 160.37 (2-C), 152.05 (1'-C), 135.20 (3'-C), 130.07 (9'-C), 129.14 (6'-C), 126.12 (8-C), 125.33 (5-C), 124.91 (6-C), 124.77 (7'-C), 122.38 (9-C), 110.56 (4-C), 19.93 (5-CH$_3$). $^1$H, $^{13}$C-HSQC (800 MHz, CDCl$_3$, cross-peaks δ): 8.28/122.38, 8.03/124.91, 7.58/126.12, 7.51/124.77, 7.38/110.57, 2.80/19.93. HRMS (ESI): calcd: 199.0866; found: 199.0864.

5-Methylnaphtho[2,1-d]oxazol-2-amine (SKA-121). SKA-121 was prepared from 4-methyl-1-tetralone according to general procedure IV. The product was isolated as brown crystals (50 mg, 4%); m.p.=186° C. dec; R$_f$=0.28 (cyclohexane-EtOAc, 1:1). $^1$H NMR (800 MHz, CDCl$_3$, δ): 8.03 (d, J=8.5 Hz, 1H, 9-H), 8.01 (d, J=8.3 Hz, 1H, 6-H), 7.56 (t, J=7.5 Hz, 1H, 7-H), 7.45 (t, J=6.0 Hz, 1H, 8-H), 7.43 (s, 1H, 4-H), 5.33 (bs, 2H, NH$_2$), 2.73 (s, 3H, CH$_3$). $^{13}$C NMR (200 MHz, CDCl$_3$, δ): 160.80 (2-C), 141.72 (1'-C), 137.24 (3'-C), 128.85 (5-C), 119.28 (6-C), 125.21 (9-C), 126.39 (7-C), 123.92 (8-C), 131.34 (6'-C), 119.77 (9'-C), 117.17 (4-C), 19.58 (5-CH$_3$). $^1$H, $^{13}$C-HSQC (800 MHz, CDCl$_3$, cross-peaks δ): 8.03/125.21, 8.01/119.28, 7.56/126.39, 7.45/123.92, 7.43/117.17, 2.73/19.58. HRMS (ESI): calcd: 199.0866; found: 199.0864.

Crystal Structure Determinations, The SKA-120 and SKA-121 crystals selected for data collection were mounted in the 90 K nitrogen cold stream provided by CRYO Industries low temperature apparatus on the goniometer head of a Bruker D8 diffractometer equipped with an ApexII CCD detector. Data were collected with the use of Mo Kα radiation (λ=0.71073 Å). The structures were solved by direct methods (SHELXS-97) and refined by full-matrix least-squares on F$^2$ (SHELXL-2013). All non-hydrogen atoms were refined with anisotropic displacement parameters. For a description of the method see (Sheldrick, 2008).

Crystal data SKA-120, C$_{12}$H$_{10}$N$_2$O, F.w.=198.22, brown plate, dimensions 0.18×0.34×0.60 mm, monoclinic, P2$_1$/n, a=14.2110(9) Å, b=3.8854(3) Å, c=17.5101(11) Å, β=107.537(2)°, V=921.89(11) Å$^3$, Z=4, R1 [1518 reflections with />2σ(/)]=0.0307, wR2 (all 1671 data)=0.0900, 176 parameters, 0 restraints.

Crystal data SKA-121, C$_{12}$H$_{10}$N$_2$O, F.w.=198.22, brown plate, monoclinic, P2$_1$/n, a=8.0532(12) Å, b=21.377(3) Å, c=11.5094(17) Å, β=107.823(2)°, V=1886.3(5) Å$^3$, Z=8, R1 [2571 reflections with />2σ(/)]=0.0376, wR2 (all 3413 data)=0.0949, 335 parameters, 0 restraints.

Cells, Cell lines and Clones. HEK-293 cells stably expressing hK$_{Ca}$2.1, rK$_{Ca}$2.2 and hK$_{Ca}$3.1 were obtained from Khaled Houamed (University of Chicago, Ill.) in 2002 and have been maintained in the Wulff laboratory at the University of California since then. The cloning of hK$_{Ca}$2.3 (19 CAG repeats) and hK$_{Ca}$3.1 has been previously described (Wulff et al., 2000). The hKCa2.3 clone was later stably expressed in COS-7 cells at Aurora Biosciences Corp., San Diego, Calif. Cell lines stably expressing other mammalian ion channels were gifts from several sources: hK$_{Ca}$1.1 in HEK-293 cells (Andrew Tinker, University College London); hK$_V$2.1 in HEK293 cells (James Trimmer, UC Davis); K$_V$11.1 (HERG) in HEK-293 cells (Craig January, University of Wisconsin, Madison); hNa$_V$1.4 in HEK-293 cells (Frank Lehmann-Horn, University of Ulm, Germany), hNa$_V$1.5 in HEK-293 cells (Christopher Lossin, University of California Davis), and hCa$_V$1.2 in HEK-293 cells (Franz Hofmann, Munich, Germany). L929 cells stably expressing mK$_V$1.3, and mK$_V$3.1 have been previously described (Grissmer et al., 1994); N1E-115 neuroblastoma cells (expressing mNa$_V$1.2) were obtained from ATCC; division arrested CHO cells expressing hNa$_V$1.7 were purchased from ChanTest (Cleveland, Ohio).

Electrophysiology. Experiments were conducted either manually with an EPC-10 amplifier (HEKA, Lambrecht/Pfalz, Germany) or on a QPatch-16 automated electrophysiology platform (Sophion Biosciences, Denmark). For manual experiments COS-7, HEK-293 or L929 cells were trypsinized, plated onto poly-L-lysine coated coverslips and typically recorded from between 20 min and 4 h after plating. Patch pipettes were pulled from soda lime glass (micro-hematocrit tubes, Kimble Chase, Rochester, N.Y.) and had resistances of 2-3 MΩ. For measurements of K$_{Ca}$ channels expressed in HEK-293 cells (K$_{Ca}$2.1, K$_{Ca}$2.2 and K$_{Ca}$3.1) we used normal Ringer as external with an internal pipette solution containing (in mM): 140 KCl, 1.75 MgCl$_2$, 10 HEPES, 10 EGTA and 7.4 CaCl$_2$ (500 nM free Ca$^{2+}$) or 6 CaCl$_2$ (250 nM free Ca$^{2+}$), pH 7.2, 290-310 mOsm. Free Ca$^{2+}$ concentrations were calculated with MaxChelator assuming a temperature of 25° C., a pH of 7.2 and an ionic strength of 160 mM. To reduce contaminating currents from native chloride channels in COS-7 cells, K$_{Ca}$2.3 currents were recorded with an internal pipette solution containing (in mM): 145 K$^+$ aspartate, 2 MgCl$_2$, 10 HEPES, 10 EGTA and 7.4 CaCl$_2$ (500 nM free Ca$^{2+}$), pH 7.2, 290-310 mOsm. Na$^+$ aspartate Ringer was used as an external solution (in mM): 160 Na$^+$ aspartate, 4.5 KCl, 2 CaCl$_2$, 1 MgCl$_2$, 5 HEPES, pH 7.4, 290-310 mOsm. Both K$_{Ca}$2 and K$_{Ca}$3.1 currents were elicited by 200-ms voltage ramps from −120 mV to 40 mV applied every 10 sec and the fold-increase of slope conductance at −80 mV by drug taken as a measure of channel activation. K$_V$2.1, Kv1.3, and K$_V$3.1 currents were recorded in normal Ringer solution with a Ca$^{2+}$-free KF-based pipette solution as previously described (Schmitz et al., 2005). HERG (K$_V$11.1) currents were recorded with a 2-step pulse from −80 mV first to 20 mV for 1 sec and then to −50 mV for 1 sec. Reduction of both peak and tail current by the drug was determined. Na$_V$1.7 currents were recorded with 30 ms pulses from −90 mV to −10 mV every 10 sec with a CsF-based pipette solution and normal Ringer as an external solution. Ca$_V$1.2 currents were elicited by 100-ms depolarizing pulses from −80 to 20 mV every 10 sec with a CsCl-based pipette solution and an external solution containing 30 mM BaCl$_2$. Blockade of both Na$^+$ and Ca$^{2+}$ currents was determined as reduction of the current minimum.

For automated electrophysiology experiments cells were grown to ~70% confluency, rinsed in sterile PBS containing 0.02% EDTA, and lifted with 2 mL of TrypLE™ Express (Gibco, Grand Island, N.Y.) for ~2 min. When cells were rounded but not detached, they were dislodged by gentle tapping, suspended in DMEM, centrifuged and resuspended in 1 ml of external solution, placed into the Qfuge tube and resuspended in 150-200 μL extracellular solution after one additional spin on the QPatch. Whole-cell patch-clamp experiments were then carried out using disposable 16-channel planar patch chip plates (QPlates; patch hole diameter approximately 1 μm, resistance 2.00±0.02 MΩ). Cell positioning and sealing parameters were set as follows: positioning pressure −70 mbar, resistance increase for success 750%, minimum seal resistance 0.1 GΩ, holding potential −80 mV, holding pressure −20 mbar. In order to avoid rejection of cells with large $K_{Ca}3.1$ currents the minimum seal resistance for whole-cell requirement was lowered to 0.001 GΩ. Access was obtained with the following sequence: 1) suction pulses in 29 mbar increments from −250 mbar to −453 mbar; 2) a suction ramp of an amplitude of −450 mbar; 3) −400 mV voltage zaps of 1 ms duration (10×). Following establishment of the whole-cell configuration, cells were held at −80 mV and $K_{Ca}3.1$, $K_{Ca}2.1$ or $K_{Ca}2.2$ currents elicited by a voltage protocol that held at −80 mV for 20 ms, stepped to −120 mV for 20 ms, ramped from −120 to 40 mV in 200 ms and then stepped back to −120 mV for 20 ms. This pulse protocol was applied every 10 s. $K_{Ca}1.1$ currents were elicited by 160-ms voltage ramps from −80 to 80 mV applied every 10 sec (500 nM free $Ca^{2+}$), and channel modulation measured as a change in mean current amplitude. $Na_V1.2$ currents from N1E-115 cells, $Na_V1.4$ and $Na_V1.5$ currents from stably transfected HEK cells were recorded with 20 ms pulses from −90 mV to 0 mV every 10 sec with a KF-based internal solution and normal Ringer as an external solution. Current slopes (in ampere per sec) were measured using the SophionQPatch software and exported to Microsoft Excel and Origin 7.0 (OriginLab Corp. MA) for analysis. Increases or decreases of slopes between −85 and −65 mV were used to calculate $K_{Ca}2/3$ activation. Data fitting to the Hill equation to obtain $EC_{50}$ and $IC_{50}$ values was performed with Origin 7.0. Data are expressed as mean±SD.

The inside-out experiments shown in FIG. 4 were performed on the $K_{Ca}3.1$-stable HEK 293 cell line. Symmetrical $k^+$ was used to obtain larger currents. The extracellular solutions contained (in mM): 154 KCl, 10 HEPES (pH=7.4), 2 $CaCl_2$, 1 $MgCl_2$. Solutions on the intracellular side contained (in mM): 154 KCl, 10 HEPES (pH=7.2), 10 EGTA, 1.75 $MgCl_2$ and $CaCl_2$ to yield calculated free $Ca^{2+}$-concentrations of 0.05, 0.1, 0.25, 0.3, 0.5, 1, and 10 μM. Cells were clamped to a holding potential of at 0 mV and $K_{Ca}$ currents were elicited by 200-ms voltage-ramps from −80 to 80 mV applied every 10 sec.

For all electrophysiology experiments solutions of benzothiazoles and benzooxazoles were always freshly prepared from 1 mM or 10 mM stock solutions in DMSO during the experiment. The final DMSO concentration never exceeded 1%. For automated assays glass vial inserts (Sophion Biosciences, Denmark) were filled with 350-400 μL of compound solution and placed into the glass insert base plate for use in the QPatch assay right before starting the QPatch.

Isometric Myography on Porcine Coronary Arteries (PCA). PCA were carefully dissected from hearts kindly provided by the local abattoir (Mercazaragoza, Zaragoza, Spain), cleaned of fat and connective tissue, and cut into 3-4 mm rings. Rings were mounted on hooks connected to an isometric force transducer (Pioden UF1, Graham Bell House, Canterbury, UK) and were pre-stretched to an initial tension of 1 g. Composition Krebs buffer (in mM): NaCl 120, $NaHCO_3$ 24.5, $CaCl_2$ 2.4, KCl 4.7, $MgSO_4$ 1.2, $KH_2PO_4$ 1 and glucose 5.6, pH 7.4, at 37° C. and equilibrated with 95% $O_2$/5% $CO_2$. Changes in tension were registered using a Mac Lab System/8e program (AD Instruments Inc., Milford, Mass.). The buffer contained the NO-synthase blocker, Nω-nitro-L-arginine (L-NNA, 300 μM), and the cyclooxygenase blocker indomethacin (10 μM) in order to measure EDH-type relaxation. After 3 washes, rings were pre-contracted the thromboxane analogue U46619 (0.2 μM). Thereafter rings were exposed to bradykinin (BK, 1 μM) in combination with either vehicle DMSO, SKA-111 (1 μM), SKA-111 plus TRAM-34 (1 μM), SKA-111 plus TRAM-34 plus UCL-1684 (1 μM), SKA-121 (1 μM), SKA-121 plus TRAM-34, SKA-121 plus TRAM-34 plus UCL-1684. After washout, rings were contracted with a high KCl buffer (60 mM) to determine maximal contraction. TRAM-34 was synthesized as previously described (Wulff et al., 2000). UCL1684 and U46619 were purchased from Tocris (Wiesbaden-Nordenstadt, Germany). Data analysis: EDH-type relaxations were determined as % change of U46619 contraction and are shown relative to the totally relaxed state (w/o U46619).

Telemetry. The experiments were in accordance with the ARRIVE guidelines and approved by the Institutional Animal Care and Use Committee of the IACS. Surgical implantation of TA11PA-C10 pressure transducers (Data Sciences International (DSI), St. Paul, Minn., USA) into the left carotid artery and telemetry were performed as described previously (Brahler et al., 2009). Four female wild-type (22±1 g) and four female KCa3.1$^{-/-}$ (27±2 g) mice were used in the present study. After surgery, mice were allowed to recover for 10 days before compounds or vehicle were injected and telemetry data were collected. After a wash-out phase of at least 48 h after a first injection, animals were re-used for injections of a higher dose of the SKA-111, SKA-121, or vehicle. Thereafter, mice were treated with 50 microgr/ml Nω-nitro-L-arginine methyl ester (L-NAME, Sigma-Aldrich, DK) in the drinking water. This L-NAME treatment over 2 days increased mean blood pressure (MAP) by 10±2 mm Hg in wild-type mice. Injection of compounds started on the 3$^{rd}$ day of the L-NAME treatment. Preparation and injection of SKA-111 and SKA-121: Appropriate amounts of SKA-111 and SKA-121 were dissolved in warmed peanut oil (SKA-111) or in a mixture of peanut oil/DMSO (9:1 v/v, both from Sigma-Aldrich, DK) to give a dose of 30 or 100 mg/kg. Maximal injection volume was ≤600 μl. SKA-111 solution, well-stirred suspension (SKA-121), or vehicles were injected i.p. during the 3$^{rd}$ h of the dark phase. Mice were subjected to isoflurane anesthesia to minimize stress and pain during compound application. Telemetry data were collected and analyzed after the mice fully recovered from anesthesia (20 min after injection). Telemetry data were recorded over 1 minute every 10 minutes over 24 h and averaged. Data were analyzed using the DSI software.

Pharmacokinetics. Twelve week-old male C57Bl/6Jmice were purchased from Charles River Laboratories (Wilmington, Mass.) and housed in microisolator cages with rodent chow and autoclaved water ad libitum. All experiments were in accordance with National Institutes of Health guidelines and approved by the University of California, Davis, Institutional Animal Care and Use Committee. For intravenous application SKA-111 and SKA-121 were dissolved at 5 mg/mL in a mixture of 10% CremophorEL (Sigma-Aldrich, St. Louis, Mo.) and 90% phosphate-buffered saline and then injected at 10mg/kg into the tail vein (n=8 mice per compound). Another group of mice (n=8) received SKA-121 orally. At various time points after the injection blood was collected into EDTA blood sample collection tubes either from the saphenous vein or by cardiac puncture under deep isoflurane anesthesia. Following the cardiac puncture mice were sacrificed by cutting the heart and then the brain was removed. Individual mice were typically used for 3 times points (2 blood collections from the saphenous vein plus the terminal blood collection). Plasma was separated by centrifugation and plasma and brain samples were stored at −80° C pending analysis. Brain samples were homogenized in 1 ml of $H_2O$ with a Brinkman Kinematica PT 1600E homogenizer and the protein precipitated with 1 ml of acetonitrile. The samples were then centrifuged at 3000 rpm and supernatants concentrated to 1 ml. Plasma and homogenized brain samples were purified using C18 solid phase extraction cartridges (ThermoFisher Scientific, Waltham, Mass., USA) preconditioned with acetonitrile followed by 1 ml of water. The loaded column was washed with 2 ml of water. SKA-121 was eluted with 3 ml of acetonitrile. SKA-111 was eluted with 3 ml of methanol containing 1% $NH_4OH$. Eluted fractions were dried under nitrogen and reconstituted in acetonitrile. LC/MS analysis was performed with a Waters Acquity UPLC (Waters, New York, N.Y.) equipped with a Acquity UPLC BEH 1.7 µm RP-18 column (Waters, New York, N.Y.) interfaced to a TSQ Quantum Access Max mass spectrometer (MS) (ThermoFisher Scientific, Waltham, Mass., USA). The isocratic mobile phase consisted of 80% acetonitrile and 20% water, both containing 0.1% formic acid with a flow rate of 0.25 ml/min. Under these conditions SKA-111 had a retention time (RT) of 0.83 min and SKA-121 a RT of 0.96 min. Using electrospray ionization MS and selective reaction monitoring (SRM) (capillary temperature 300° C., capillary voltage 4000 V, collision energy −34 eV, positive ion mode), SKA-121 was quantified by its base peak of 128.14 m/z and its concentration was calculated with a 5-point calibration curve from 100 nM to 10 µM. SKA-111 (capillary temperature 325° C., capillary voltage 4000 V, collision energy −28eV, positive ion mode) was quantified by its base peak of 200.045 m/z and its concentration was calculated with a 6-point calibration curve from 100 nM to 20 µM.

The percentage of plasma protein binding for SKA-111 and SKA-121 was determined by ultrafiltration. Rat plasma (500 µl) was spiked with 10 µM of compound in 1% dimethylsulfoxide and the sample loaded onto a Microcon YM-30 Centrifugal Filter (Millipore Corp., Bedford, Mass., USA) and centrifuged at 13,500 g for 30 minutes at room temperature. The retentate was collected by inverting the filter into an Eppendorf tube and spinning at 13,500 g for 15 minutes. The retentate then underwent sample preparation as per the above-described procedure for SKA-111 or SKA-121. Plasma protein binding was found to be to be 59±2% (n=3) for SKA-111 and 81±4% (n=2) for SKA-121.

Results

Figure 1:
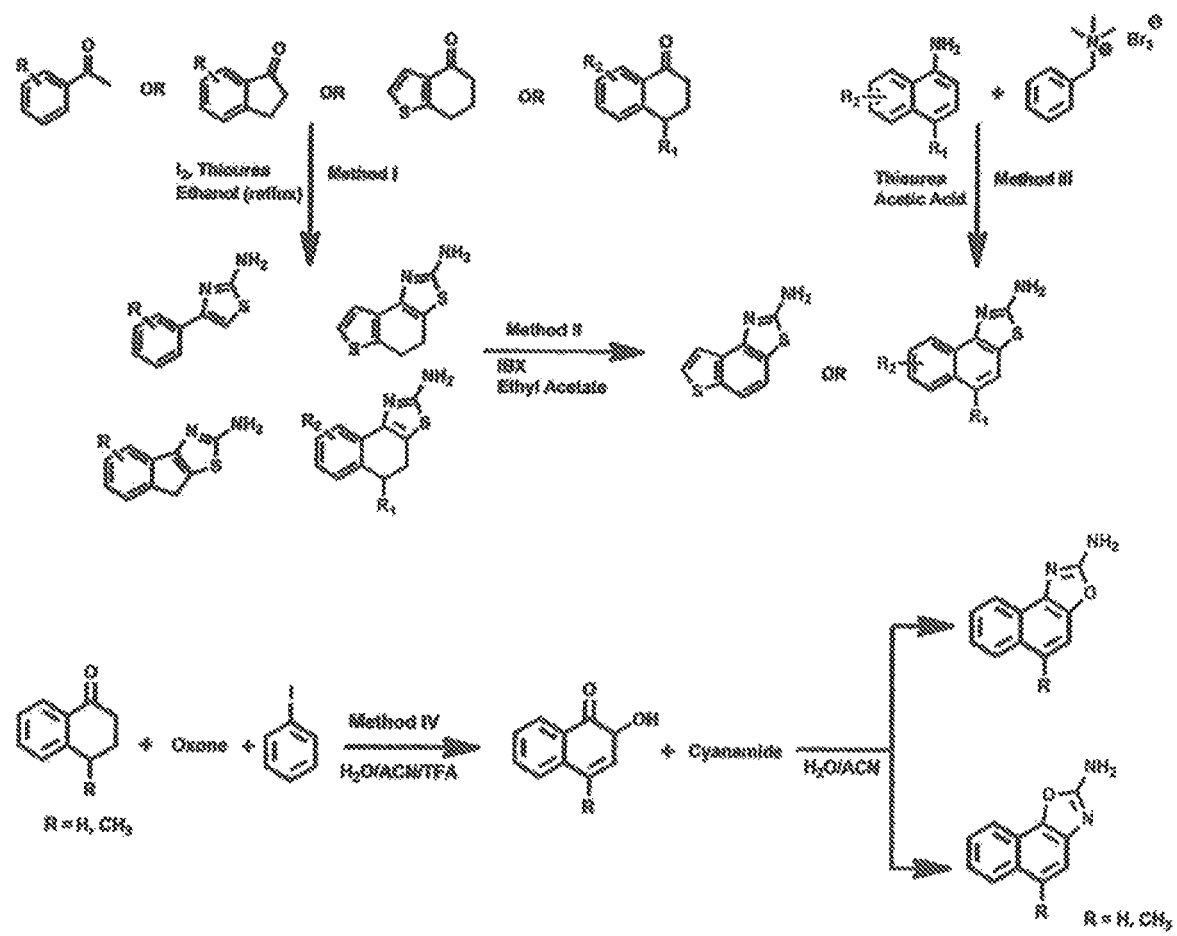
FIG. 1 shows a general scheme for the synthesis of thiazoles, 2-aminonaphtho[1,2-d]thiazoles and 2-aminonaphtho[1,2-d]oxazoles.

SAR Study Aiming to Obtain Selectivity for $K_{Ca}3.1$ with SKA-31 as a Template. The limited ability of existing benzimidazole/benzothiazole-type $K_{Ca}2/3$ activators such as SKA-31 to differentiate between $K_{Ca}2$ and $K_{Ca}3.1$ channels made it desirable to try if additional structural modification would increase selectivity for $K_{Ca}3.1$. Towards this goal we synthesized a small focused library of 2-aminothiazoles, 2-aminobenzothiazoles or 2-aminonapthooxazoles (FIG. 1). Substituted 2-aminothiazoles were prepared by a one-step Hantzsch thiazole synthesis (Goblyos et al., 2005) from the appropriate substituted 1-tetralone, thiourea, and iodine (Method I in FIG. 1). This method allowed us to obtain both "open" 2-aminothiazoles as well as to replace the central aromatic ring of SKA-31 with aliphatic rings. Fully aromatic 2-aminobenzothiazoles could then be produced by aromatizing with 2-iodoxybenzoic acid (IBX) (Method II in FIG. 1). An alternative route to 5-position substituted 2-aminobenzothiazole was the classic Hugerschoff benzothiazole synthesis (Jordan et al., 2003) in which appropriately substituted amines were transformed into the corresponding thioureas and then subsequently reacted with benzyl trimethyl ammonium tribromide to deliver bromine in stoichiometric amounts as an alternative to liquid bromine (Method III in FIG. 1). Lastly, naphthooxazoles were prepared by first oxidizing 4-methyl-1-tetralone with in-situ formed bis(trifluoroacetoxy)iodo]benzene and then adding cyanamide (Schuart et al., 1973) to the intermediately produced 4-methylnaphthalene-1,2-dione (Method IV in FIG. 1).

The compounds synthesized by these methods as well as five commercially available compounds were tested for their $K_{Ca}2.3$ and $K_{Ca}3.1$ activating activity using either manual or automated whole-cell patch-clamp. Our group previously described the establishment of a QPatch assay for $K_{Ca}3.1$ modulators. In this study we benchmarked data obtained on the QPatch against manual patch-clamp electrophysiology by determining the potency of several commonly used $K_{Ca}3.1$ inhibitors (TRAM-34, NS6180, charybdotoxin) and activators (EBIO, riluzole, SKA-31) and found that the QPatch results were virtually identical to the IC50 and $EC_{50}$ values obtained by manual patch-clamp in our hands (Jenkins et al., 2013). We here made use of this assay and determined $EC_{50}$ values for $K_{Ca}3.1$ activation using HEK-293 cells stably expressing human $K_{Ca}3.1$. Activities on human $K_{Ca}2.3$ were determined by manual electrophysiology since we currently only have $K_{Ca}2.3$ available in COS-7 cells, which are difficult to handle on the QPatch. For both channels we used 250 nM of free $[Ca^{2+}]_i$ since positive gating-modulators like SKA-31 typically increase $K_{Ca}$ currents at this $Ca^{2+}$ concentration roughly 30-fold creating a large assay window (Jenkins et al., 2013; Sankaranarayanan et al., 2009).

Figure 2:
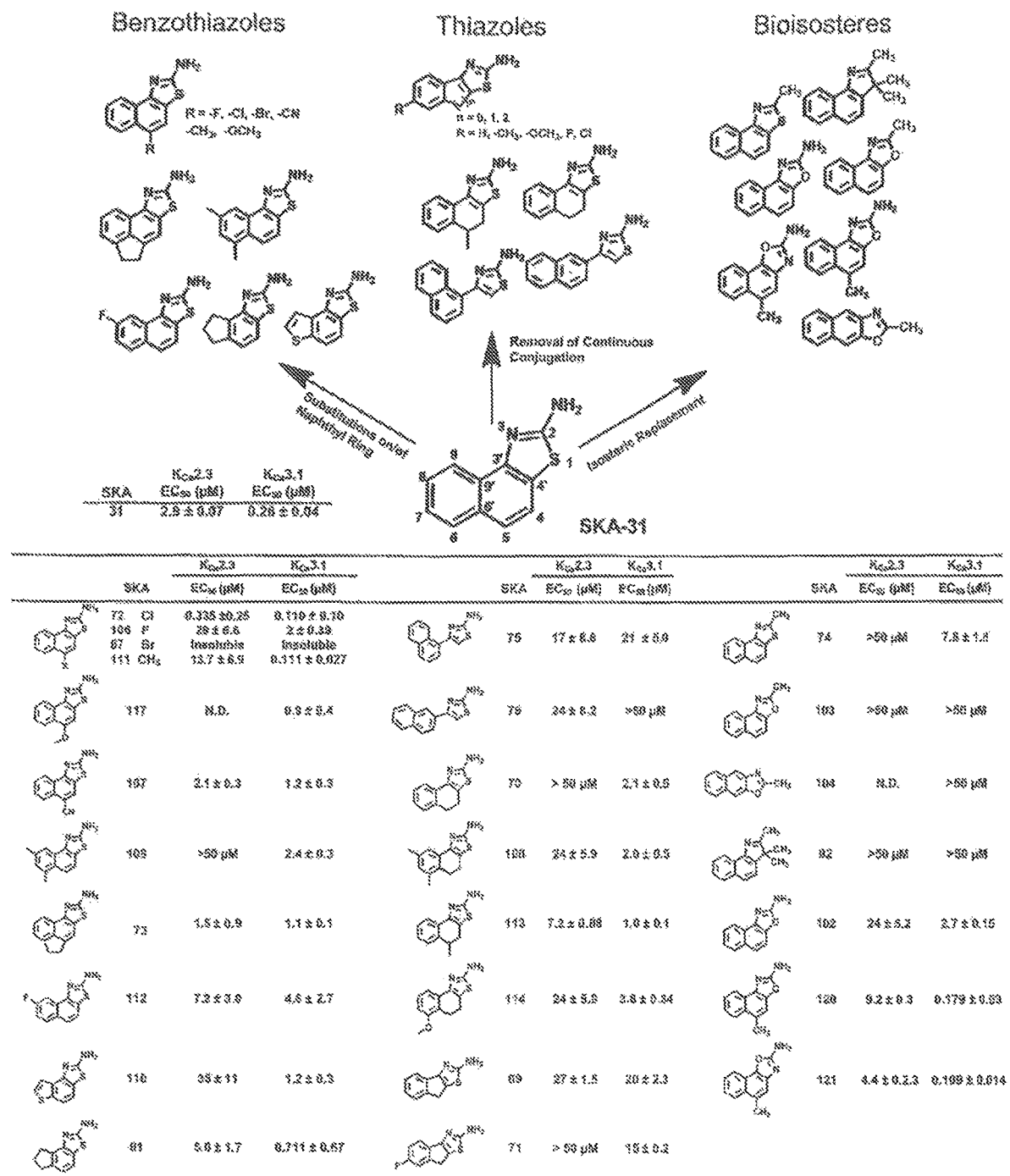
FIG. 2 shows chemical structures and $EC_{50}$ values for $K_{Ca}2.3$ and $K_{Ca}3.1$ activation. All compounds were tested at least 3 times at 4 to 5 concentrations and $EC_{50}$ values determined by fitting the Hill equation to the increase in slope conductance between −80 and −65 mV.

Removal of the continuous conjugation by opening of the napthothiazole system (SKA-75 and SKA-76) of SKA-31 or replacement of the internal aromatic ring with either a cyclohexyl (SKA-70, SKA-108, SKA-113, SKA-114) or a cyclopentyl ring (SKA-69, SKA-71) in general reduced both potency and selectivity irrespective of whether the compounds bore any substituents or not (FIG. 2 blue compounds). Since these results demonstrated that aromaticity of the internal ring was required for both $K_{Ca}2.3$ and $K_{Ca}3.1$ activation, we went back to benzothiazoles (FIG. 2 green compounds) and next explored substitutions on the napthothiazole system of SKA-31. Introduction of substituents in 5-position had varying effects: Chloride (SKA-72), which is both electron withdrawing and lipophilic, increased potency on both $K_{Ca}2.3$ ($EC_{50}$ 335 nM) and $K_{Ca}3.1$ ($EC_{50}$ 110 nM) but basically abolished any selectivity between the two channels. Fluoride in 5-position (SKA-106) reduced potency roughly 10-fold compared with SKA-31 but preserved selectivity, while introduction of bromide (SKA-87) resulted in a compound that was too insoluble to be tested. Introduction of a methyl group in 5-position, which is less lipophilic than chloride but has a positive inductive effect on the ring system, slightly increased potency for $K_{Ca}3.1$ ($EC_{50}$ 111 nM) in comparison to SKA-31 and dramatically increased selectivity for $K_{Ca}3.1$ over $K_{Ca}2.3$ to ~100-fold (SKA-111). However, replacement of the $CH_3$ group with other, larger carbon containing electron-donating groups such as —$OCH_3$ (SKA-117) or electron withdrawing groups such as —CN (SKA-107) again reduced potency and selectivity. Attaching two of the obviously favorable $CH_3$ groups in positions 6 and 8 of the ring system (SKA-109) instead of the 5-position preserved selectivity over $K_{Ca}2.3$ but reduced potency on $K_{Ca}3.1$ by 10-fold. Installation of an ethylene bridge connecting the 5 and 6 position reduced both potency and selectivity and resulted in a compound (SKA-73) that activated both $K_{Ca}2.3$ and $K_{Ca}3.1$ equipotently with an $EC_{50}$ of 1 µM. We further tried replacing the terminal ring of SKA-31 with a thiophene (SKA-110) or an aliphatic cyclopentyl (SKA-81) but again only saw a reduction in potency.

Figure 3:
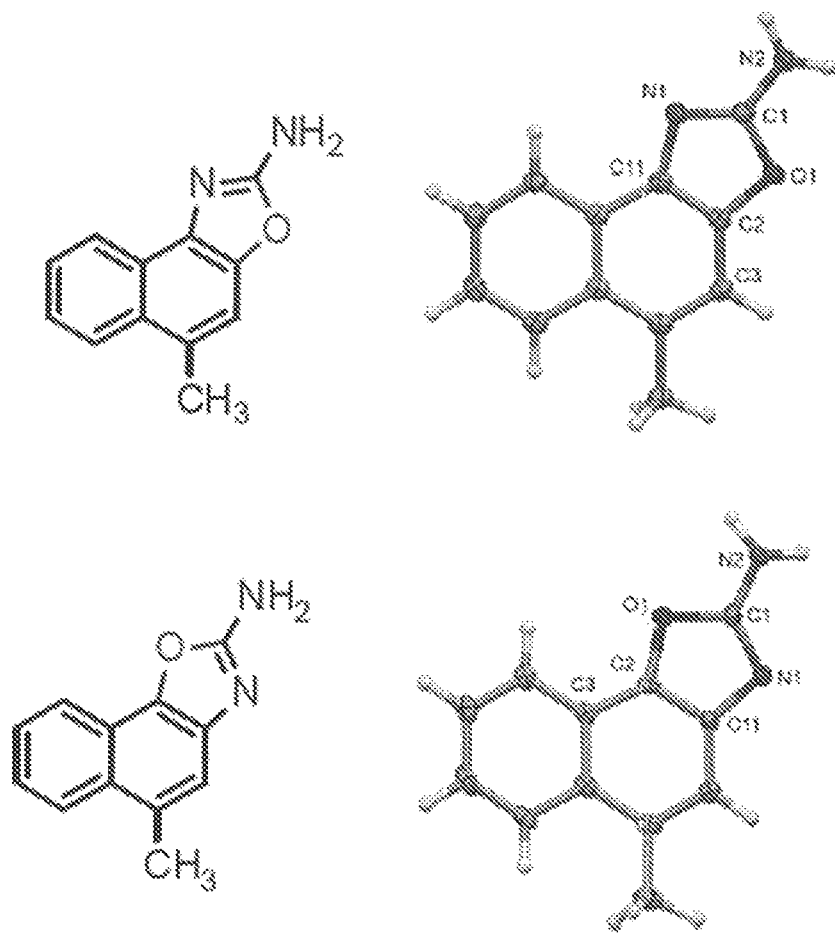
FIG. 3 shows X-ray crystal structures of SKA-120 and SKA-121.

To better understand the full extent of the pharmacophore and potentially obtain patentable compounds we explored alternative scaffolds (FIG. 2 red compounds). Moving away from the 2-aminothiazole system by replacing the 2-position $NH_2$ group with a $CH_3$ group (SKA-74) as well as isosterically replacing the S atom with an O (SKA-103 and SKA-104) or geminal $CH_3$ groups (SKA-92) completely abolished activity. However, if the 2-position $NH_2$ group was retained and only the S isosterically replaced with an O as in the SKA-102, which basically constitutes an oxazole analogous SKA-31, activity was regained and the resulting compound activated $K_{Ca}3.1$ with an $EC_{50}$ of 2.7 µM. Introduction of a $CH_3$ group in 5-position, which had previously been found to increase selectivity of the napthothiazole SKA-111 for $K_{Ca}3.1$ to 100-fold, had a similar effect on the 2-aminonaphthooxazole system. The two regioisomers, SKA-120 and SKA-121, which resulted from the synthesis and had to be separated by flash chromatography, exhibited $EC_{50}$ values of 180 and 109 nM for $K_{Ca}3.1$ and $EC_{50}$ values of 9.2 and 4.4 µM for $K_{Ca}2.3$, corresponding to a ~50 or 40-fold selectivity. The correct structural assignment of the two regioisomers was confirmed by the different chemical shift of proton 9-H in the 800 MHz $^1$H-NMR, since this proton is shielded differently depending on whether it is in proximity to either N or O in the adjacent oxazole ring. We further grew crystals of SKA-120 and SKA-121 and had them subjected to X-ray analysis, which allowed us to "see" the exact position of the N and O in the two compounds (FIG. 3). The crystal structures show two very different hydrogen bonding networks. While SKA-120 exists as a dimer, SKA-121 has a hydrogen bonding motif that leads to a tetramer forming ribbon structures (Supplementary FIG. 1).

In summary, this SAR study demonstrated that it is possible to generate $K_{Ca}3.1$-selective activators using the naphthothiazole and the isosteric naphthooxazole scaffolds. In both cases the presence of the 2-amino group was absolutely required for activity on both $K_{Ca}2.3$ and $K_{Ca}3.1$ channels. It was further necessary for the annulated 3-ring system to be fully aromatic. Replacement of the terminal or the internal ring system with aliphatic rings reduced activity on both channels. The key position able to confer both high potency and selectivity for $K_{Ca}3.1$ seems to be the 5 position, which proved to have a very "tight" SAR. While the large, lipophilic and relatively "soft" chloride endowed the compounds with potency on both $K_{Ca}2.3$ and $K_{Ca}3.1$ (SKA-72), only $CH_3$ in this position produced selectivity for KCa3.1 on both the naphthothiazole (SKA-111) and the isosteric naphthooxazole (SKA-121) system.

SKA-111 and SKA-121 are Selective KCa3.1 Activators. To fully evaluate the selectivity of the naphthothiazole SKA-111 and the naphthooxazole SKA-121, we determined 7-point concentration-response curves on $K_{Ca}2.1$, $K_{Ca}2.2$, $K_{Ca}2.3$ and $K_{Ca}3.1$ with 250 nM free $Ca^{2+}$ in the internal solution (FIG. 4). SKA-111 and SKA-121 displayed nearly identical $EC_{50}$ values on $K_{Ca}3.1$ (111±27 nM and 109±14 nM). Similar to the template SKA-31 (Sankaranarayanan et al., 2009), these effects plateaued at a roughly 30-fold maximal current increase with this intracellular $Ca^{2+}$ concentration. Both compounds exhibited 40 to 120-fold selectivity over the three $K_{Ca}2$ channels (FIG. 4 and Table 1, below).

TABLE 1

Selectivity of SKA-111 and SKA-121 over selected ion channels

| Channel | SKA-111 $EC_{50}$ | SKA-121 $EC_{50}$ |
|---|---|---|
| $K_{Ca}1.1$ | 120% of current at 25 µM (3) | 115% of current at 50 µM (3) |
| $K_{Ca}2.1$ | 8.1 ± 0.4 (10) | 8.7 ± 1.6 (8) |
| $K_{Ca}2.2$ | 7.7 ± 1.9 (10) | 6.8 ± 1.7 (12) |
| $K_{Ca}2.3$ | 13.7 ± 6.9 (15) | 4.4 ± 2.6 (18) |
| $K_{Ca}3.1$ | 0.111 ± 0.027 (24) | 0.019 ± 0.014 (21) |

| Channel | SKA-111 % current inhibition at 25 µM | SKA-121 % current inhibition at 50 µM |
|---|---|---|
| $K_V1.3$ | 28.5 ± 2.3% (4) | 27.5 ± 7.2% (3) |
| $K_V2.1$ | 37.3 ± 9.0% (4) | 43.2 ± 12.5% (3) |
| $K_V3.1$ | 32.9 ± 1.3% (3) | 46.3 ± 16.5% (4) |
| $K_V11.1$ (hERG) | 10.1 ± 7.7% (5) | 16.7 ± 9.7% (5) |
| $Na_V1.2$ | 19.5 ± 6.9% (5) | 15.2 ± 12.7% (5) |
| $Na_V1.4$ | 33.4 ± 10.5% (5) | 25.7 ± 1.3% (5) |
| $Na_V1.5$ | 39.9 ± 11.1% (5) | 32.1 ± 11.1% (5) |
| $Na_V1.7$ | 27.5 ± 0.9% (3) | 28.5 ± 1.8% (5) |
| $Ca_V1.2$ | 49.5 ± 17.0% (5) | 48.9 ± 2.7% (5) |

The number in brackets indicates the number of cells used to determining the $EC_{50}$ values or the % of current inhibition.

The Hill coefficient $n_H$ varied between 1.6 and 3.1 in most cases, which was again similar to what had been previously reported for the template SKA-31.

We next determined the selectivity of SKA-111 and SKA-121 over more distantly related channels. At the highest reasonable and well dissolvable test concentrations, 25 µM for SKA-111 and 50 µM for SKA-121, both compounds blocked representative members of the major $K_V$ channel families ($K_V1.3$, $K_V2.1$, $K_V3.1$ and $K_V11.1$) by 10 to 46% (Table 1). Similarly, neuronal ($Na_V1.2$, $Na_V1.7$), skeletal muscle ($Na_V1.4$), and cardiac ($Na_V1.5$) sodium channels as well as L-type $Ca^{2+}$ channels ($Ca_V1.2$) were blocked by 20 to 50% by 25 µM of SKA-111 or 50 µM SKA-121. SKA-111 and SKA-121 thus displayed at least 200 to 400-fold selectivity for $K_{Ca}3.1$ over these physiologically relevant channels.

Figure 4A:
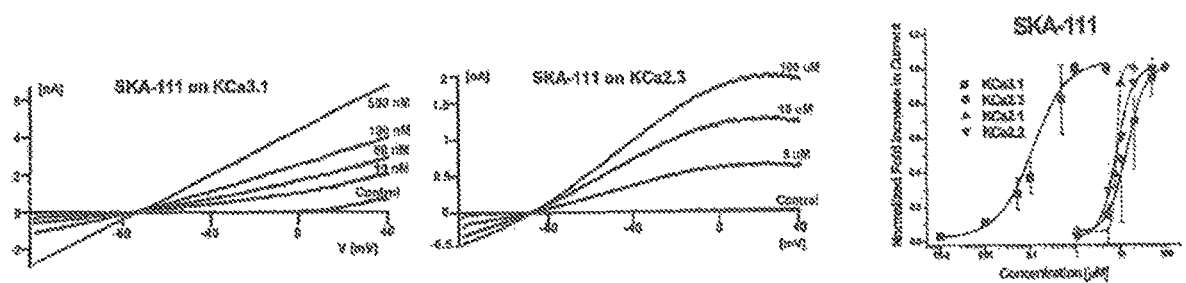
FIGS. 4A-4F are graphs showing effects of SKA-111 and SKA-121 on certain potassium channels and indicating that SKA-111 and SKA-121 are potent and selective $K_{Ca}3.1$ activators.
Figure 4B:
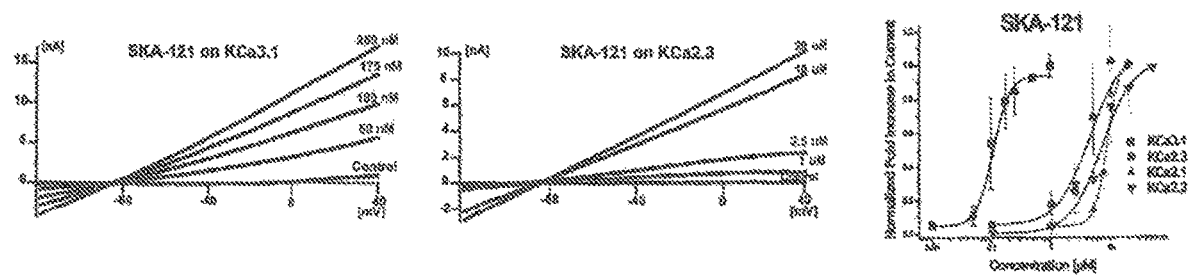
Figure 4C:
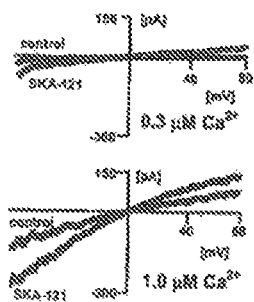
Figure 4D:
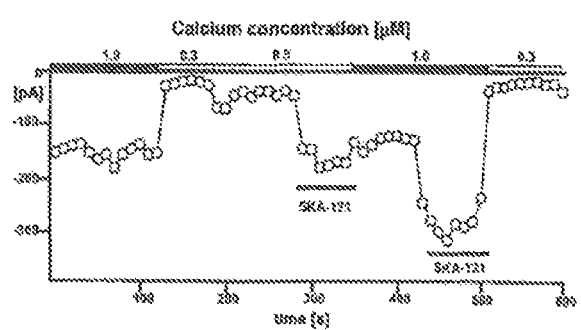
Figure 4E:
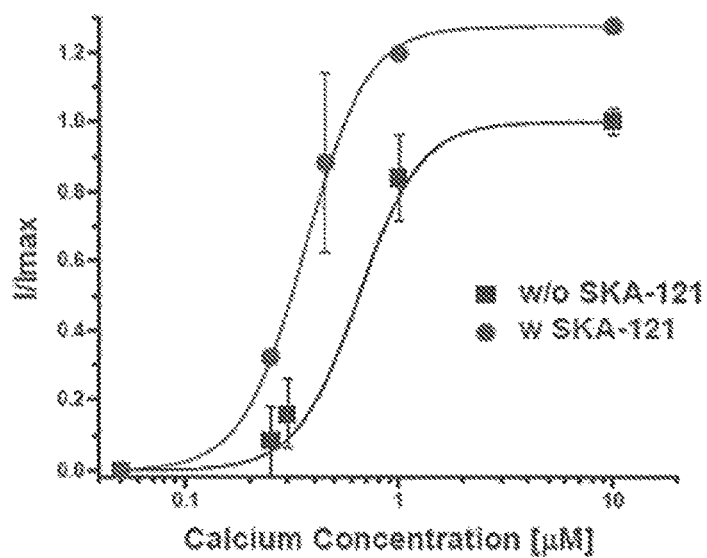
Figure 4F:
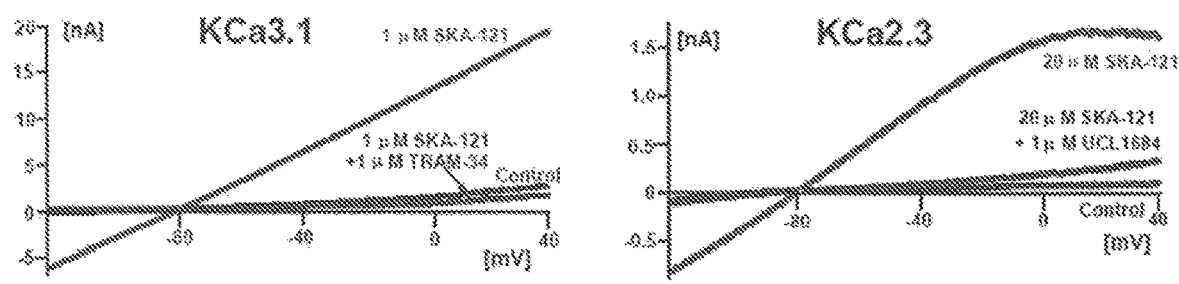

SKA-121 is a Positive Gating Modulator of KCa3.1. Classic $K_{Ca}$ activators like EBIO and NS309 have been shown to increase the apparent $Ca^{2+}$-sensitivity of $K_{Ca}$ channels by stabilizing the interaction between CaM and $K_{Ca}$ channels (Li et al., 2009; Pedarzani et al., 2001). Since this phenomenon manifests in a leftward shift of the $Ca^{2+}$ concentration-response curve we performed inside-out experiments in which we varied the intracellular $[Ca^{2+}]_i$ concentration and investigated the ability of 1 µM of SKA-121 to further activated $K_{Ca}3.1$ currents at the different $[Ca^{2+}]_i$ concentrations. As shown in FIG. 4C, inside-out patches pulled from $hK_{Ca}3.1$-expressing HEK-293 cells exhibited $Ca^{2+}$-dependent $K^+$ currents reversing at 0 mV in symmetrical $K^+$, which could be increased further by SKA-121 at every $Ca^{2+}$ concentration. The $EC_{50}$ of the $Ca^{2+}$-concentration response curve (FIG. 4E) shifted from 650±50 nM to 360±110 nM in presence of 1 µM of SKA-121, while the Hill coefficient was not changed by SKA-121 ($n_H$ ~3 in both cases). Interestingly, SKA-121 did not only shift the curve to the left but also increased the maximal achievable current at 1 and 10 µM, suggesting that the compound might be able to further increase the open probability of $K_{Ca}3.1$ at these $Ca^{2+}$ concentrations. As expected, $K_{Ca}3.1$ currents activated by 1 µM SKA-121 could be completely inhibited by 1 µM of the $K_{Ca}3.1$ pore blocker TRAM-34 (Wulff et al., 2000), while the $K_{Ca}2$ channel pore blocker UCL1684 (Rosa et al., 1998) had a similar effect on $K_{Ca}2.3$ currents activated by 20 µM SKA-121 (FIG. 4F).

Figure 5A:
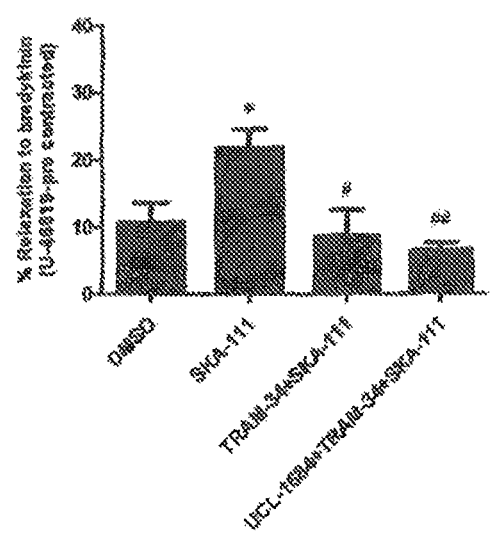
FIGS. 5A and 5B are bar graphs showing isometric myography in isolated tissues following exposure to either control (DMSO) or different doses of either 1) SKA-111 (FIG. 5A) or SKA-121 (FIG. 5B) alone, 2) SKA-111 (FIG. 5A) or SKA-121 (FIG. 5B) in combination with just TRAM-34 or 3) SKA-111 (FIG. 5A) or SKA-121 (FIG. 5B) in combination with both TRAM-34 and UCL-1684. As shown, SKA-111 and SKA-121 alone (both at 1 µM) increased bradykinin-induced EDH-type relaxation of U46619-precontracted porcine coronary artery rings in the presence of blockers of NO-synthesis (L-NNA) and cyclooxygenases (indomethacin). The co-administration of TRAM-34 (1 µM) alone and the co-administration of TRAM-34+UCL-1684 (1 µM) prevented the increase of relaxation. Data are mean±SEM, n=5-22 PCA. *<0.05, unpaired Student T-test.
Figure 5B:
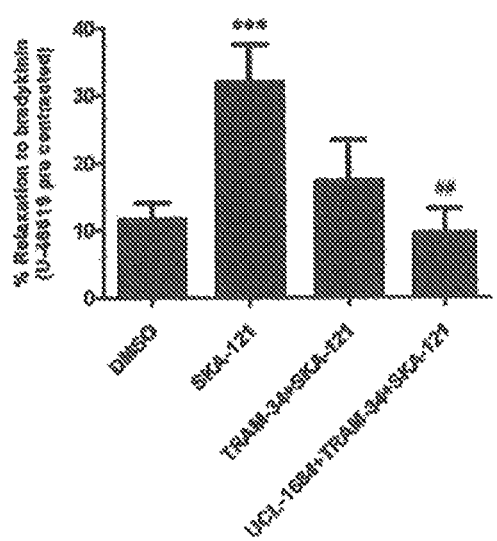

SKA-111 and SKA-121 Increase Bradykinin Induced Vasodilation. In addition to modulating the contractile state of the underlying vascular smooth muscle by releasing nitric oxide and prostacyclin, the vascular endothelium can also induce an endothelium-derived hyperpolarization (EDH) in response to stimulation with acetylcholine or bradykinin (BK). These agonists increase $[Ca^{2+}]_i$ in the endothelium, activate $K_{Ca}3.1$ and $K_{Ca}2.3$ and induce $K_{Ca}$ channel mediated hyperpolarization and arterial relaxation (Dalsgaard et al., 2010; Edwards et al., 2010; Grgic et al., 2009; Köhler et al., 2010; Ng et al., 2008; Wulff and Köhler, 2013). To demonstrate that SKA-111 and SKA-121 efficiently augment native $K_{Ca}3.1$ in porcine coronary arteries (PCA) and thereby potentiate BK-induced relaxation we performed isometric myography on PCA pre-contracted with 0.2 µM of the vasospasmic thromboxane mimetic, U46619. SKA-111 as well as SKA-121, both at 1 µM, potentiated BK (1 µM)-induced relaxation to ≈200 and ≈300%, respectively (FIG. 5). The $K_{Ca}3.1$ blocker TRAM-34 (1 µM) prevented this potentiation and the combination of TRAM-34 and the $K_{Ca}2.3$ blocker UCL-1684 (1 µM) inhibited this potentiation slightly more effectively than TRAM-34 alone (FIG. 5).

These data from ex-vivo vessel experimentation demonstrate that the $K_{Ca}3.1$-selective activators SKA-111 and SKA-121 are capable of positively modulating a physiological response, e.g. EDH-type vasorelaxation, in which $K_{Ca}3.1/K_{Ca}2.3$ functions have been implicated before (Edwards et al., 2010; Wulff and Köhler, 2013).

Figure 6A:
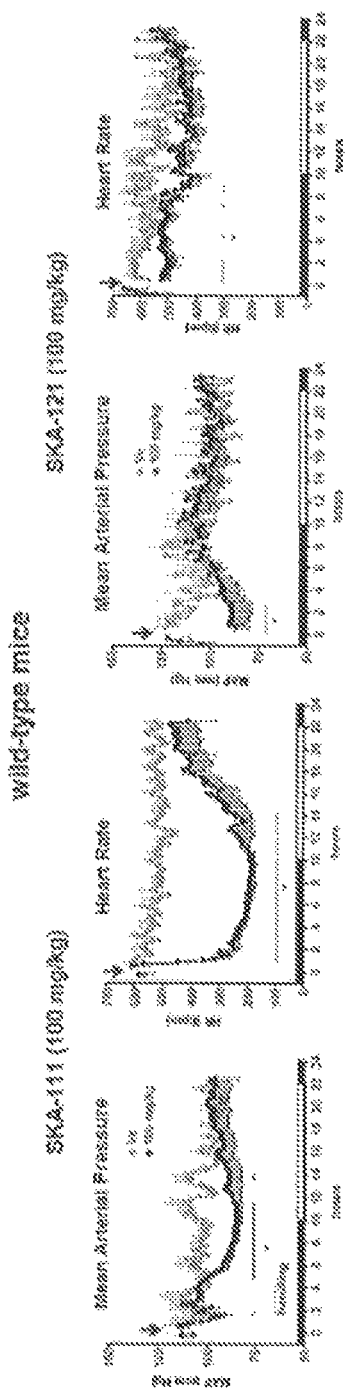
FIGS. 6A-6C are graphs showing mean arterial blood pressure and heart rate versus time in mice following administration of either SKA-111 or SKA-121.

Systemic cardiovascular effects of SKA-111 and SKA-121: Since we had mice implanted with telemetry leads available we performed telemetric blood pressure measurements on wild-type and $K_{Ca}3.1^{-/-}$ mice to evaluate the cardiovascular activity and selectivity of SKA-111 and SKA-121 before performing pharmacokinetic studies. However, since we did not know the half-live when these experiments were done, we chose to start with the relatively high dose of 100 mg/kg for both compounds reasoning that we could lower the dose in subsequent experiments. In wild-type mice, i.p. injection of 100 mg/kg SKA-111 produced a substantial drop in mean arterial blood pressure (MAP) by ~25 mmHg starting 20-30 min after injection (FIG. 6A left). This decrease in MAP was significant when compared to vehicle (peanut oil)-treated mice. The blood pressure drop was accompanied by a severe reduction of heart rate (HR) by ~400 bpm (FIG. 6A left). To avoid fatal hypothermia or circulatory collapse, we handled these severely bradycardic mice for ~2 h and increased RT to 34° C. As shown in FIG. 6A these maneuvers increased MAP transiently, presumably because of a sympathetic input on total peripheral resistance, but not HR and the low HR persisted over another 10 h before the mice slowly recovered (FIG. 6A left). SKA-121 at 100 mg/kg also lowered blood pressure by ~20 mmHg (FIG. 6A right). However, this drop was more transient and lasted for ~3 h. HR was only moderately reduced (FIG. 6A right). A lower dose of 30 mg/kg of both compounds did not produce significant alterations in MAP (Suppl. FIG. 3), while SKA-111 decreased HR to a minor extent (~–50 bpm for ~2 h after injection (Suppl. FIG. 3). The vehicles, peanut oil (for SKA-111) or peanut oil/DMSO (9:1 v/v, for SKA-121) did not cause significant alterations of MAP or HR (FIG. 6A).

Figure 6B:
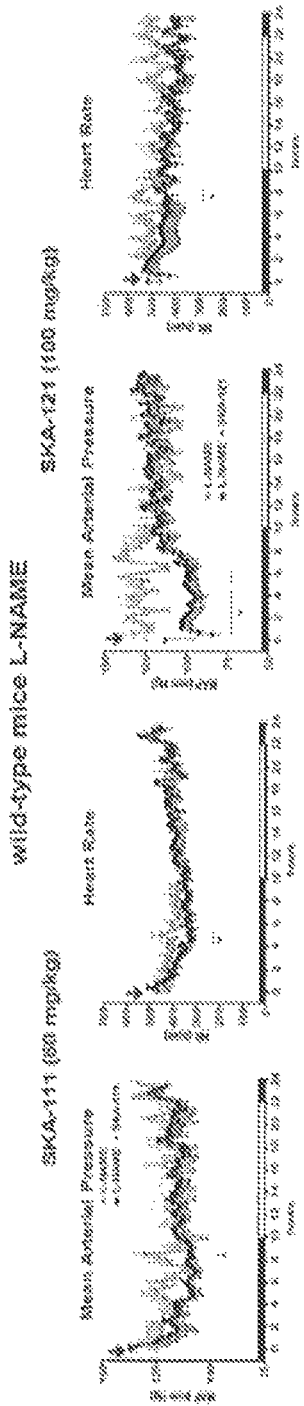

We next tested whether SKA-111 and SKA-121 are also efficient in lowering the higher MAP caused by systemic inhibition of nitric oxide production by L-NAME administered in the drinking water (FIG. 6B). However, for these experiments we used a lower dose (60 mg/kg) of SKA-111 to avoid causing such a severe drop of HR as observed with 100 mg/kg. The 60 mg/kg dose produced only a minor drop in MAP and HR. In contrast, SKA-121 at 100 mg/kg produced a significant drop in MAP by ~25 mm Hg over 6 h. This drop was accompanied by a minor decrease in HR (FIG. 6B right).

Figure 6C:
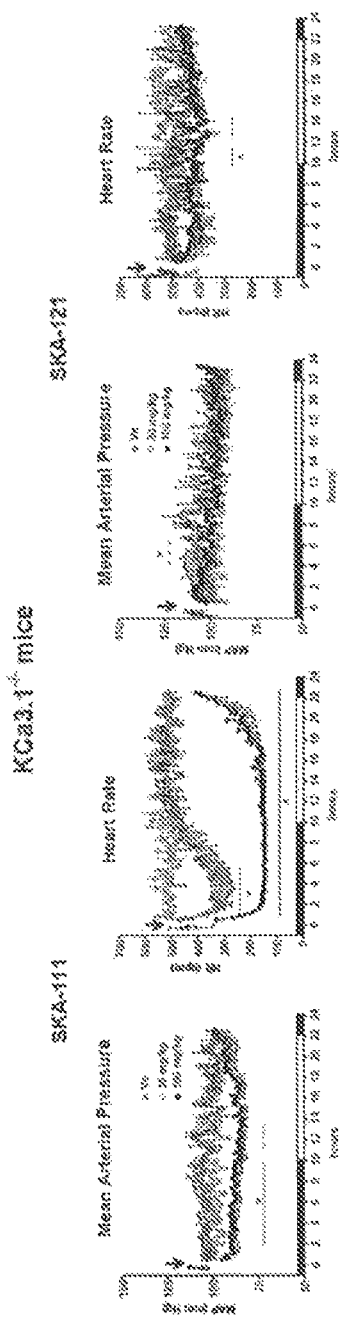

We next evaluated the $K_{Ca}3.1$ selectivity by using KCa3.1$^{-/-}$ mice and found that SKA-111 at 100 mg/kg also produced a significant drop in MAP by ~15 mmHg lasting for ~16 h in these animals (FIG. 6C left). Similar to wild-type mice, HR decreased substantially by ~400 bpm over ~22 h (FIG. 6C left). Similar to wild-type mice the lower dose of 30 mg/kg also significantly reduced HR, although less dramatically and not for such a long time as the higher dose. MAP did not change with the 30 mg/kg dose of SKA-111 (FIG. 6C left). In contrast to SKA-111, SKA-121 at 100 mg/kg had no significant effects on MAP and HR in the $K_{Ca}3.1^{-/-}$ mice (FIG. 6C right).

Taken together, these telemetry experiments showed that both compounds exhibited cardiovascular activity in vivo as they substantially reduce basal blood pressure and the higher blood pressure caused by NO deficiency. Moreover, SKA-121 produced this blood pressure lowering actions in a $K_{Ca}3.1$-dependent manner as suggested by lack of MAP-lowering effects in $K_{Ca}3.1^{-/-}$ mice. In contrast, SKA-111 lowered MAP and induced a strong HR reduction independently of $K_{Ca}3.1$.

Pharmacokinetics of SKA-111 and SKA-121. In order to help us to better interpret the results of the telemetry experiments we established UPLC/MS assays for SKA-111 and SKA-121 based on a HPLC/MS assay we had previously published for SKA-31 (Sankaranarayanan et al., 2009) and performed some basic pharmacokinetic studies with both compounds in mice. Following intravenous injection at 10 mg/kg into the tail vein, total SKA-111 plasma concentrations fell bi-exponentially reflecting a 2-compartment model with very rapid distribution from blood into tissue (~2 min) followed by elimination with a half-life of 4.7±0.6 h (FIG. 7A). SKA-121 in contrast had a much shorter half-live (~20 min) and plasma decay was extremely rapid (21.3±2.4 µM at 5 min; 483±231 nM at 1 h and 53±44 nM at 4 h). Since SKA-121 is relatively well soluble (logP=1.79) and could potentially be added to drinking water in animal experiments we also administered it orally and found that it had an oral availability of roughly 25% (FIG. 7B). But again, plasma levels dropped rapidly from 1.1±0.1 µM at 1 h after oral administration to 27±5 nM at 8 h. Plasma protein binding was found to be 59±2% (n=3) for SKA-111 and 81±4% (n=2) for SKA-121. Since we had also removed brains from the mice when obtaining blood samples by cardiac puncture (which had been done at every 3$^{rd}$ blood collection), we further determined total brain concentrations at various time points and obtained averaged brain/plasma ratios for both compounds from times when the compounds were detectable in both plasma and brain. SKA-111 proved to be highly brain penetrant with a brain/plasma ratio of 9.3±5.3. SKA-121 was less brain penetrant but still very effectively partitioned into the brain with a brain/plasma ratio of 3.3±2.9 (FIG. 7C).

Taken together, these results explain why SKA-111 had a much more prolonged blood pressure lowering effect in the telemetry experiments in FIG. 6 than SKA-121. The fact that SKA-111 is highly brain penetrant and probably achieved total brain concentrations in the range of 10-30 µM for hours following i.p. administration at 100 mg/kg also provides an explanation for why this $K_{Ca}3.1$ selective compound "lost"

its selectivity in vivo and reduced blood pressure and heart rate, side-effects that are presumably mediated by $K_{Ca}2$ channel activation in the CNS as well as $K_{Ca}2$ channel activation in resistance-arteries and the heart (Radtke et al, 2013), and which also occurred in $K_{Ca}3.1^{-/-}$ mice (FIG. 6C left). In keeping with its shorter half-live of only 20 min and its lower brain penetration, SKA-121 induced a significant but less prolonged drop in MAP in the telemetry experiments when administered i.p. at 100 mg/kg (FIG. 6A right) and exhibited $K_{Ca}3.1$ selectivity in vivo as suggested by the lack of MAP-lowering effects in $K_{Ca}3.1^{-/-}$ mice and its insignificant effect on heart rate in wild-type mice.

Discussion

We here used our previously described mixed $K_{Ca}2/3$ channel activator SKA-31 (Sankaranarayanan et al., 2009) as a template for the design of two selective $K_{Ca}3.1$ activators. Both molecules, SKA-111 and SKA-121, activate $K_{Ca}3.1$ with $EC_{50}$s of ~110 nM and display 40-120 fold selectivity for $K_{Ca}3.1$ over the three $K_{Ca}2$ channels ($K_{Ca}2.1$, $K_{Ca}2.2$ and $K_{Ca}2.3$). The compounds constitute the first pharmacological or chemical biology tools that can be used to selectively activate $K_{Ca}3.1$ channels in tissue preparations or in vivo without performing additional manipulations such as genetically knocking-out or pharmacologically blocking $K_{Ca}2$ channels.

According to the definition of "positive-gating modulation" compounds like EBIO and NS309 act by shifting the $Ca^{2+}$-activation curve of $K_{Ca}2/3$ channels to the left meaning that the determined $EC_{50}$ values for $Ca^{2+}$-dependent channel activation calculated from $Ca^{2+}$-concentration response curves decrease in the presence of the modulator molecule. For NS309, studies using CaM mutants making unstable association with the CaMB of $K_{Ca}2.2$ have shown that NS309 increases the apparent $Ca^{2+}$-sensitivity of $K_{Ca}$ channels by stabilizing the interaction between CaM and the CaMBD of the $K_{Ca}$ channels (Li et al., 2009; Pedarzani et al., 2001). More recently, Zhang et al. crystallized CaM bound to the CaMBD of $K_{Ca}2.2$ and afterwards soaked EBIO info the crystal (Zhang et al., 2012). In a subsequent study the same group obtained a co-crystal of the CaM/CaMBD with NS309 (Zhang et al., 2013). Both molecules reside in a pocket formed at the interface between CaM/CaMBD. Interestingly, upon NS309 binding, an intrinsically disordered stretch of 16 amino acids, which connects S6 to the CaMBD and which was not visible in the EBIO/CaM/CaMBD crystal, becomes visible suggesting that it undergoes a transition to a well-defined structure. Other manipulations of this S6-CaMBD linker region such as cross-linking a residue in the region to a residue in the CaMBD also increase channel activity and apparent $Ca^{2+}$ sensitivity demonstrating that this linker region plays a crucial role in coupling $Ca^{2+}$ binding to CaM to the mechanical opening of $K_{Ca}$ channels (Zhang et al., 2013). By changing the confirmation of this linker region NS309 is thus "truly" a gating modulator and we assume that SKA-111 and SKA-121 are exerting their effects in a similar manner. We have not yet mapped their binding sites but have made the observation that mutations of the analogous residues in the CaMBD of $K_{Ca}2.3$, which had been reported to increase or decrease the potency of EBIO for activating $K_{Ca}2.2$ (Zhang et al., 2012), also significantly altered the potency of SKA-31 (Brown et al., 2014) suggesting that similar to EBIO and NS309 benzothiazole-type $K_{Ca}2/3$ activators bind at the interface between CaM/CaMBD. This interface pocket is relatively "tight" and the CaMBD shows a number of sequence differences between the four $K_{Ca}$ channels making if appear plausible that a "minor" structural change such as adding a —$CH_3$ in 5-position of SKA-31 can increase selectivity for $K_{Ca}3.1$ from 10-fold to 100-fold in SKA-111. This hypothesis that SKA-31, SKA-111 and SKA-121 are binding to the same site in the CaM/CaMBD interface as NS309 agrees well with the relatively steep structure-activity-relationship we observed in our study. For the napthobenzothiazole and the isostericnaphthooxazole system potency and selectivity for $K_{Ca}3.1$ over $K_{Ca}2$ channels was very sensitive to the exact position and electronic nature of substituents (e.g. SKA-106 and SKA-109 in FIG. 2). Another interesting observation in this context is that SKA-121 did not only shift the concentration-response curve for $Ca^{2+}$-dependent $K_{Ca}3.1$ activation to the left but also increased the maximal achievable current at 1 and 10 µM in inside-out patches (FIG. 4). Since none of the benzothiazole-type $K_{Ca}2/3$ activators including SKA-31, SKA-111, SKA-121 and their many derivatives had ever increased $K_{Ca}3.1$ or $K_{Ca}2$ currents in our hands at $Ca^{2+}$ concentrations lower than 100 nM or in the absence of $Ca^{2+}$ with KF based pipette solutions, we do not ascribe this effect to a directly channel opening component in their mechanism of action like has been reported for GW542573X and (-)-CM-TMPF for $K_{Ca}2.1$ (Hougaard et al., 2012; Hougaard et al., 2009). Unlike SKA-121, which we think is binding at the CaM/CaMBD interface, (-)CM-TMPF has been found to interact with positions deep within the inner pore vestibule (Hougaard et al., 2012) close to the selectivity filter, where the gate of $K_{Ca}2/3$ channels seems to be located (Bruening-Wright et al., 2007; Bruening-Wright et al., 2002; Garneau et al., 2009; Klein et al., 2007). It therefore seems reasonable to attribute the $Ca^{2+}$-independent $K_{Ca}2.1$ channel activation by (-)-CM-TMPF to a directly opening effect on the gate and use this explanation to account for the fact that (-)-CM-TMPF increases $K_{Ca}2.1$ currents to roughly 40% of their maximal activity at $Ca^{2+}$ concentrations between 10 and 100 nM and then levels off in its opening/activating activity at higher $Ca^{2+}$ concentrations (Hougaard et al., 2012). Since this is clearly not the case for SKA-121, which in contrast further increases maximal channel activity at 1 and 10 µM of $Ca^{2+}$, we believe that SKA-121 is a "classic" positive gating modulator, which requires the presence of $Ca^{2+}$ in order to enhance $K_{Ca}$ channel activity but which by stabilizing the interaction between CaM and the CaMBD of $K_{Ca}3.1$ is also able to further increase the $Ca^{2+}$-dependent open channel probability $P_o(max)$ value of $K_{Ca}3.1$. Unlike $K_{Ca}2$ channels, which are assumed to be fully open at saturating $[Ca_{2+}]_i$ concentrations, $K_{Ca}3.1$ channels have been reported to have a relatively low $Ca^{2+}$-dependent $P_o(max)$ which can be increased significantly by the addition of 1.6 mM MgATP (Gerlach et al., 2001; Jones et al., 2007) or by mutations of residues in S5 (Garneau et al., 2014). We here left out ATP from the internal solutions for inside-out and whole-cell recordings on purpose to not confuse the analysis by having too many variables.

Since $K_{Ca}3.1$ is involved in EDH-mediated vasodilator responses and has been accordingly suggested as a potential new antihypertensive pharmacological target (Dalsgaard et al., 2010; Edwards et al., 2010; Grgic et al., 2009; Köhler et al., 2010), we tested the effect of both of our new $K_{Ca}3.1$ selective activators, SKA-111 and SKA-121, on BK-induced EDH responses in vitro on porcine coronary arteries and on blood pressure in mice. Both compounds potentiated BK effects in vitro and robustly lower blood pressure in mice in vivo. However, as these experiments and subsequently performed pharmacokinetic studies showed, both compounds do not have ideal properties for development into a potential antihypertensive drug candidate. SKA-111 is so highly brain penetrant that it achieves roughly ~10-fold higher concentrations in the CNS and may thus cause complex neurological side-effects by activating neuronal $K_{Ca}2$ channels (Adelman et al., 2012). Moreover, SKA-111 induces the same severe bradycardia which had also been a problem when the unselective SKA-31 was dosed at 100 mg/kg in connexin 40-deficient mice (Radtke et al., 2013). This bradycardia is especially impressive in that it occurs also in KCa3.1$^{-/-}$ mice (FIG. 6) and is probably due to direct effects on $K_{Ca}2$ channels in cardiac pacemaker tissue (Radtke et al., 2013) as well as a possible a central decrease in sympathetic drive through activation of neuronal $K_{Ca}2$ channels. SKA-121 is less brain penetrant and largely maintains its $K_{Ca}3.1$ selectivity in vivo. It lowers blood pressure in both normotensive and hypertensive mice without significantly reducing heart rate or affecting blood pressure in $K_{Ca}3.1^{-/-}$ mice. However, a problem with SKA-121 is the extremely short 20-min half-life in mice, which would necessitate continuous infusion for blood pressure studies, a depot, or very frequently repeated drug applications. But in this respect, it should of course be explored if SKA-121 possibly has a longer half-life in larger animals such as dogs, pigs or primates.

In summary, with SKA-111 and SKA-121 we have identify two $K_{Ca}3.1$-selective positive gating modulators which constitute novel pharmacological tools for further dissecting the role of $K_{Ca}3.1$ in EDH and systemic blood pressure and which could help determine whether $K_{Ca}3.1$ activators could eventually be developed into a new class of endothelial targeted antihypertensives. Other potential indications for $K_{Ca}3.1$ activators could be intra-surgical hypertension, acute vasospasm, or preservation of endothelial function in large vascular organs like hearts or kidneys or in vessel grafts during storage and transplantation. $K_{Ca}3.1$ activators have also long been suggested for enhancing fluid secretion in cystic fibrosis (Singh et al., 2001). Although SKA-111 and SKA-121 are not ideal candidate molecules they could serve as templates for the design of derivatives such as the ones claimed in this invention with pharmacokinetic properties more suitable for further development and innovation.

It is to be appreciated that, although the invention has been described hereabove with reference to certain examples or embodiments of the invention, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the substantial absence of other elements, steps, members, components, compositions, reactants, parts or portions unless otherwise noted. All reasonable additions, deletions, modifications and alterations are to be considered equivalents of the described examples and embodiments and are to be included within the scope of the following claims.

References

Adelman J P, Maylie J, and Sah P (2012) Small-conductance $Ca^{2+}$-activated $K^+$ channels: form and function. *Ann Rev Physiol* 74: 245-269.

Balut C M, Hamilton K L, and Devor D C (2012) Trafficking of intermediate (KCa3.1) and small (KCa2.x) conductance, $Ca^{2+}$-activated $K^+$ channels: a novel target for medicinal chemistry efforts? *ChemMedChem* 7: 1741-1755.

Blank T, Nijholt I, Kye M J, Radulovic J, and Spiess J (2003) Small-conductance, $Ca^{2+}$-activated $K^+$ channel SK3 generates age-related memory and LTP deficits. *Nat Neurosci* 6: 911-912.

Brahler S, Kaistha A, Schmidt V J, Wolfle S E, Busch C, Kaistha B P, Kacik M, Hasenau A L, Grgic I, Si H, Bond C T, Adelman J P, Wulff H, de Wit C, Hoyer J, and Köhler R (2009) Genetic deficit of SK3 and IK1 channels disrupts the endothelium-derived hyperpolarizing factor vasodilator pathway and causes hypertension. *Circulation* 119: 2323-2332.

Brown B M, Coleman N, Oliván-Viguera A, Köhler R, Wulff H (2014) Positive KCa channel gating modulators with selectivity for KCa3.1. *FASEB J* 28:1057.6

Bruening-Wright A, Lee W S, Adelman J P, and Maylie J (2007) Evidence for a deep pore activation gate in small conductance $Ca^{2+}$-activated $K^+$ channels. *J Gen Physiol* 130: 601-610.

Bruening-Wright A, Schumacher M A, Adelman J P, and Maylie J (2002) Localization of the activation gate for small conductance $Ca^{2+}$-activated $K^+$ channels. *J Neurosci* 22: 6499-6506.

Dalsgaard T, Kroigaard C, and Simonsen U (2010) Calcium-activated potassium channels—a therapeutic target for modulating nitric oxide in cardiovascular disease? *Expert Opin Ther Targets* 14: 825-837.

Damkjaer M, Nielsen G, Bodendiek S, Staehr M, Gramsbergen J B, de Wit C, Jensen B L, Simonsen U, Bie P, Wulff H, and Köhler R (2012) Pharmacological activation of KCa3.1/KCa2.3 channels produces endothelial hyperpolarization and lowers blood pressure in conscious dogs. *Br J Pharmacol* 165: 223-234.

Debono M W, Le Guern J, Canton T, Doble A, and Pradier L (1993) Inhibition by riluzole of electrophysiological responses mediated by rat kainate and NMDA receptors expressed in *Xenopus* oocytes. *Eur J Pharmacol* 235: 283-289.

Devor D C, Singh A K, Frizzell R A, and Bridges R J (1996) Modulation of Cl$^-$ secretion by benzimidazolones. I. Direct activation of a Ca$^+$-dependent K$^+$ channel. *Am J Physiol* 271: L775-784.

Duprat F, Lesage F, Patel A J, Fink M, Romey G, and Lazdunski M (2000) The neuroprotective agent riluzole activates the two P domain K$^+$ channels TREK-1 and TRAAK. *Mol Pharmacol* 57: 906-912.

Edwards G, Feletou M, and Weston A H (2010) Endothelium-derived hyperpolarising factors and associated pathways: a synopsis. *Pflugers Arch* 459: 863-879.

Fanger C M, Ghanshani S, Logsdon N J, Rauer H, Kalman K, Zhou J, Beckingham K, Chandy K G, Cahalan M D, and Aiyar J (1999). Calmodulin mediates calcium-dependent activation of the intermediate conductance KCa channel, IKCa1. *J Biol Chem* 274: 5746-5754.

Garneau L, Klein H, Banderali U, Longpre-Lauzon A, Parent L, and Sauve R (2009) Hydrophobic interactions as key determinants to the KCa3.1 channel closed configuration. An analysis of KGa3.1 mutants constitutively active in zero $Ca^{2+}$. *J Biol Chem* 284: 389-403.

Garneau L, Klein H, Lavoie M F, Brochiero E, Parent L, and Sauve R (2014) Aromatic-aromatic interactions between residues in KCa3.1 pore helix and S5 transmembrane segment control the channel gating process. *J Gen Physiol* 143: 289-307.

Gerlach A C, Syme C A, Giltinan L, Adelman J P, and Devor D C (2001) ATP-dependent activation of the intermediate conductance, $Ca^{2+}$-activated $K^+$ channel, hIK1, is conferred by a C-terminal domain. *J Biol Chem* 276: 10963-10970.

Goblyos A, Santiago S N, Pietra D, Mulder-Krieger T, von Frijtag Drabbe Kunzel J, Brussee J, and Ijzerman A P (2005) Synthesis and biological evaluation of 2-aminothiazoles and their amide derivatives on human adenosine receptors. Lack of effect of 2-aminothiazoles as allosteric enhancers. *Bioorg&Med Chem* 13: 2079-2087.

Grgic I, Kaistha B P, Hoyer J, and Köhler R (2009) Endothelial $Ca^{2+}$-activated $K^+$ channels in normal and impaired EDHF-dilator responses-relevance to cardiovascular pathologies and drug discovery. *Br J Pharmacol* 157: 509-526.

Grissmer S, Nguyen A N, Aiyar J, Hanson D C, Mather R J, Gutman G A, Karmilowicz M J, Auperin D D, and Chandy K G (1994) Pharmacological characterization of five cloned voltage-gated $K^+$ channels, types Kv1.1, 1.2, 1.3, 1.5, and 3.1, stably expressed in mammalian cell lines. *Mol Pharmacol* 45: 1227-1234.

Grunnet M, Jespersen T, Angelo K, Frokjaer-densen C, Klaerke D A, Olesen S P, and Jensen B S (2001) Pharmacological modulation of SK3 channels. *Neuropharmacol* 40: 879-887.

Hougaard C, Eriksen B L, Jorgensen S, Johansen T H, Dyhring T, Madsen L S, Strobaek D, Christophersen P (2007). Selective positive modulation of the SK3 and SK2 subtypes of small conductance $Ca^{2+}$-activated $K^+$ channels. *Br J Pharmacol* 151: 655-665.

Hougaard C, Hammami S, Eriksen B L, Sorensen U S, Jensen M L, Strobaek D, and Christophersen P (2012) Evidence for a common pharmacological interaction site on K(Ca)2 channels providing both selective activation and selective inhibition of the human K(Ca)2.1 subtype. *Mol Pharmacol* 81: 210-219.

Hougaard C, Jensen M L, Dale T J, Miller D D, Davies D J, Eriksen B L, Strobaek D, Trezise D J, and Christophersen P (2009) Selective activation of the SK1 subtype of human small-conductance $Ca^{2+}$-activated $K^+$ channels by 4-(2-methoxyphenylcarbamoyloxymethyl)-piperidine-1-carboxylic acid tert-butyl ester (GW542573X) is dependent on serine 293 in the S5 segment. *Mol Pharmacol* 76: 569-578.

Jenkins D P, Yu W, Brown B M, Lojkner L D, and Wulff H (2013) Development of a QPatch automated electrophysioiogy assay for identifying KCa3.1 inhibitors and activators. *Assay Drug Dev Technol* 11: 551-560.

Joiner W J, Wang L Y, Tang M D, and Kaczmarek L K (1997) hSK4, a member of a novel subfamily of calcium-activated potassium channels. *Proc Natl Acad Sci USA* 94: 11013-11018.

Jones H M, Bailey M A, Baty C J, Macgregor G G, Syme C A, Hamilton K L, and Devor D C (2007) An $NH_2$-terminal multi-basic RKR motif is required for the ATP-dependent regulation of hIK1. *Channels* (Austin) 1: 80-91.

Jordan A D, Luo C, and Reitz A B (2003) Efficient conversion of substituted aryl thioureas to 2-aminobenzothiazoles using benzyltrimethylammonium tribromide. *J Org Chem* 68: 8693-8696.

Kasumu A W, Hougaard C, Rode F, Jacobsen T A, Sabatier J M, Eriksen B L, Strobaek D, Liang X, Egorova P, Vorontsova D, Christophersen P, Ronn L C, and Bezprozvanny I (2012) Selective positive modulator of calcium-activated potassium channels exerts beneficial effects in a mouse model of spinocerebellar ataxia type 2. *Chem Biol* 19: 1340-1353.

Klein H, Garneau L, Banderali U, Simoes M, Parent L, and Sauve R (2007) Structural determinants of the closed KCa3.1 channel pore in relation to channel gating: results from a substituted cysteine accessibility analysis. *J Gen Physiol* 129: 299-315.

Kohler M, Hirschberg B, Bond C T, Kinzie J M, Marrion N V, Maylie J, and Adelman J P (1996) Small-conductance, calcium-activated potassium channels from mammalian brain. *Science* 273: 1709-1714.

Köhler R (2012) Cardiovascular alterations in KCa3.1/KCa2.3-deficient mice and after acute treatment with KCa3.1/KCa2.3 activators. In: *EDHF 2012-10th Anniversary Meeting*, Feletou M, Vanhoutte P M (eds) Vol. 49, pp 1-54 Vaux-de-Cernay, France: J Vascular Research.

Köhler R, Kaistha B P, Wulff H (2010) Vascular KCa-channels as therapeutic targets in hypertension and restenosis disease. *Expert Opin Ther Targets* 14: 143-155.

Li W, Hailing D B, Hall A W, and Aldrich R W (2009) EF hands at the N-lobe of calmodulin are required for both SK channel gating and stable SK-calmodulin interaction. *J Gen Physiol* 134: 281-293.

Ng K F, Leung S W, Man R Y, and Vanhoutte P M (2008) Endothelium-derived hyperpolarizing factor mediated relaxations in pig coronary arteries do not involve Gi/o proteins. *Acta Pharmacol Sin* 29: 1419-1424.

Pedarzani P, Mosbacher J, Rivard A, Cingolani L A, Oliver D, Stocker M, Adelman J P, and Fakler B (2001) Control of electrical activity in central neurons by modulating the gating of small conductance $Ca^{2+}$-activated $K^+$ channels. *J Biol Chem* 276: 9762-9769.

Radtke J, Schmidt K, Wulff H, Köhler R, and de Wit C (2013) Activation of K 3.1 by SKA-31 induces arteriolar dilation and lowers blood pressure in normo- and hypertensive connexin40-deficient mice. *Br J Pharmacol* 170: 293-303.

Rosa J C, Galanakis D, Ganellin C R, Dunn P M, and Jenkinson D H (1998) Bisquinolinium cyclophanes: 6,10-diaza-3(1,3),8(1,4)-dibenzena-1,5(1,4)-diquinolinacyclodecaphane (UCL 1684), the first nanomolar, non-peptidic blocker of the apamin-sensitive $Ca^{2+}$-activated $K^+$ channel. *J Med Chem* 41: 2-5.

Sankaranarayanan A, Raman G, Busch C, Schultz T, Zimin P I, Hoyer J, Köhler R, and Wulff H (2009) Naphtho [1,2-d]thiazol-2-ylamine (SKA-31), a new activator of KCa2 and KCa3.1 potassium channels, potentiates the endothelium-derived hyperpolarizing factor response and lowers blood pressure. *Mol Pharmacol* 75: 281-295.

Schmitz A, Sankaranarayanan A, Azam P, Schmidt-Lassen K, Homerick D, Hansel W, and Wulff H (2005) Design of PAP-1, a selective small molecule Kv1.3 blocker, for the suppression of effector memory T cells in autoimmune diseases. *Mol Pharmacol* 68: 1254-1270.

Schuart J, and Muller H K (1973) 2-Aminooxazoles and 2-iminooxazolines. 1. Reaction of racemic alpha-methyl-aminopropiophenone using cyanobromide. *Die Pharmazie* 28: 438-439.

Sheldrick G M (2008) A short history of SHELX. *Acta Crystallographica, Section A* 64: 112-121.

Singh S, Syme C A, Singh A K, Devor D C, and Bridges R J (2001) Benzimidazolone activators of chloride secretion:

potential therapeutics for cystic fibrosis and chronic obstructive pulmonary disease. *J Pharmacol Exp Ther* 296: 600-611.

Strobaek D, Teuber L, Jorgensen T D, Ahring P K, Kjaer K, Hansen R S, Olesen S P, Christophersen P, and Skaaning-Jensen B (2004) Activation of human IK and SK $Ca^{2+}$-activated $K^+$ channels by NS309 (6,7-dichloro-1H-indole-2,3-dione 3-oxime). *Biochim Biophys Acta* 1665: 1-5.

Wei A D, Gutman G A, Aldrich R, Chandy K G, Grissmer S, and Wulff H (2005) International Union of Pharmacology. LII. Nomenclature and molecular relationships of calcium-activated potassium channels. *Pharmacol Rev* 57: 463-472.

Wulff H, and Köhler R (2013) Endothelial small-conductance and intermediate-conductance KCa channels: an update on their pharmacology and usefulness as cardiovascular targets. *J Cardiovas Pharmacol* 61: 102-112.

Wulff H, Miller M J, Haensel W, Grissmer S, Cahalan M D, and Chandy K G (2000) Design of a potent and selective inhibitor of the intermediate-conductance $Ca^{2+}$-activated $K^+$ channel, IKCa1: A potential immunosuppressant. *Proc Natl Acad Sci USA* 97: 8151-8156.

Wulff H, and Zhorov B S (2008) $K^+$ channel modulators for the treatment of neurological disorders and autoimmune diseases. *Chem Rev* 108: 1744-1773.

Xia X M, Fakler B, Rivard A, Wayman G, Johnson-Pais T, Keen J E, Ishii T, Hirschberg B, Bond C T, Lutsenko S, Maylie J, and Adelman J P (1998) Mechanism of calcium gating in small-conductance calcium-activated potassium channels. *Nature* 395: 503-507.

Zhang M, Pascal J M, Schumann M, Armen R S, and Zhang J F (2012) Identification of the functional binding pocket for compounds targeting small-conductance $Ca^{2+}$-activated potassium channels. *Nat Commun* 3: 1021.

Zhang M, Pascal J M, and Zhang J F (2013) Unstructured to structured transition of an intrinsically disordered protein peptide in coupling $Ca^{2+}$-sensing and SK channel activation. *Proc Natl Acad Sci USA* 110: 4828-4833.

Wulff H, Miller M J, Haensel W, Grissmer S, Cahalan M D, and Chandy K G (2000) Design of a potent and selective inhibitor of the intermediate-conductance $Ca^{2+}$-activated $K^+$ channel, IKCa1: A potential immunosuppressant. *Proc Natl Acad Sci USA* 97: 8151-8156.

APPENDIX A

| | SKA | KCa2.3 $EC_{50}$ (µM) | KCa3.1 $EC_{50}$ (µM) | NCE | CAS | IUPAC Name |
|---|---|---|---|---|---|---|
| 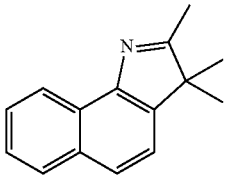 [SMILES: CC1=Nc2c(ccc3ccccc23)C1(C)C] | 92 | >50 µM | 42± | No | 74470-85-2 | 2,3,3-Trimethyl-3H-benz[g]indole; 2,3,3,-Trimethylbenz[g]indole |
| 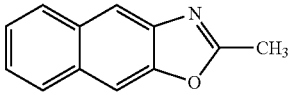 | 104 | N.D. | >50 µM | No | 20686-66-2 | 2-Methylnaphtho[2,3-d]oxadole |
| 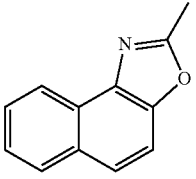 | 103 | 31± | 7.8± | No | 85-15-4 | 2-Methylnaphth(1,2-d)oxadole |
| 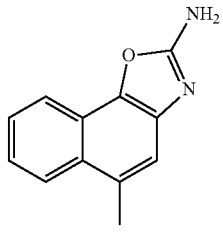 | 121 | 8± | 0.200± | Yes | | 5-methylnaphtho[2,1-d]oxazol-2-amine |
|  | 120 | 5± | 0.450± | Yes | | 5-methylnaphtho[2,1-d]oxazol-2-amine |

| | SKA | KCa2.3 EC$_{50}$ (μM) | KCa3.1 EC$_{50}$ (μM) | NCE | CAS | IUPAC Name |
|---|---|---|---|---|---|---|
| 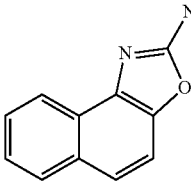 | 102 | 24± | 2.7± | No | 858432-45-8 | Naphth[1,2-d]oxadol-2-amine |
| 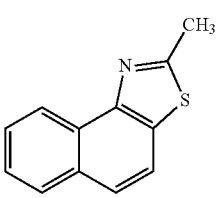 [SMILES: Nc1nc2c(ccc3ccccc32)o1] | 74 | 31± | 7.8± | No | 2682-45-3 | 2-Methylnaphtho[1,2-d]thiazole 2-Methyl-β-naphthothiazole |

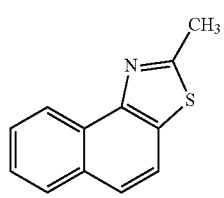

1. Compositions for regulating or modulating quorum sensing in bacteria, methods of using the compounds, and methods of regulating or modulating quorum sensing in bacteria
By Wang, Binghe; Ni, Nanting; Wang, Junfeng; Lu, Chung-Dar; Chou, Han-Ting; Li, Minyong; Zheng, Shilong; Cheng, Yunfeng; Peng, Hanjing
From PCT Int. Appl. (2009), WO 2009029317 A2 20090305, Language: English, Database: CAPLUS 2. Cyclometalated tricyclic benzofuro-, benzothio- and naphtho-annelated azole platinum-group metal complexes as phosphorescent compounds for electroluminescence devices with increased lifespan, efficiency and color purity
By Suh, Dong-Hack; Lim, Jin-Soo; Kim, Ji-Ho; Chol, Sun-Hyun
From PCT Int. Appl. (2007), WO 2007078184 A1 20070712, Language: English, Database: CAPLUS 3. Triplet emitter having condensed five-membered rings
By Johannes, Hans-Hermann; Kowalsky, Wolfgang; Ammermann, Sven; Kroener, Michael; Weinaug, Ute Jana
From PCT Int. Appl. (2007), WO 2007028822 A1 20070315, Language: English, Database: CAPLUS 4. Triplett emitter having condensed five-membered rings
By Johannes, Hans-Hermann; Kowalsky, Wolfgang; Ammermann, Sven; Kroener, Michael; Weinaug, Ute Jana
From PCT Int. Appl. (2007), WO 2007028417 A1 20070315, Language: English, Database: CAPLUS 5. Preparation of 2-alkylbenzothiazoles from 2-halonitrobenzenes
By Sakagami, Shigeki; Iida, Yukio
From Jpn. Kokai Tokkyo Koho (2006), JP 2006315979 A 20061124, Language: Japanese, Database: CAPLUS 6. Bis-transition-metal-chelate-probes
By Ebright, Richard H.; Ebright, Yon W.
From PCT Int. Appl. (2003), WO 2003091689 A2 20031106, Language: English. Database: CAPLUS 7. Lightfast indolenine-type cyanine dyes, their intermediates, and optical recording media therewith
By Ono, Takao; Naruse, Shoichiro; Tsuchiya, Masahiro
From Jpn. Kokai Tokkyo Koho (2003), JP 2003171571 A 20030620, Language: Japanese, Database: CAPLUS 8. Gordona sp. CYKS1 (KCTC 0431BP) capable of desulfurizing fossil fuel containing organic sulfur compounds
By Chang, Yong Keun; Chang, Ho Nam; Rhee, Sung-Keun; Chang, Je Hwan; Sung, Jung Hyun
From U.S. (2001), U.S. Pat. No. 6,204,046 B1 20010320, Language: English, Database: CAPLUS 9. Nocardia sp. CKYS2 (KCTC 0432Bp) capable of desulfurizing fossil fuel containing organic sulfur compounds
By Chang, Yong Keun; Chang, Ho Nam; Rhee, Sung-Keun; Chang, Je Hwan; Sung, Jung Hyun
From U.S. (2001), U.S. Pat. No. 6,197,570 B1 20010306, Language: English, Database: CAPLUS 10. Benzazole derivatives as insect and ectoparasite repellents
By Bouvier, Jacques; Christinaz, Catherine; Froelich, Olivier
From PCT Int. Appl. (1999), WO 9965866 A1 19991223, Language: English, Database: CAPLUS 11. Silver halide photographic material containing styryl compound as sensitizing dye
By Hioki, Takanori
From Jpn. Kokai Tokkyo Koho (1999), JP 11216872 A 19990810, Language: Japanese, Database: CAPLUS 12. Near IR-sensitive photoimageable/photopolymarizable compositions
By Weed, Gregory Charles; Fabricius, Dietrich Max
From Eur. Pat. Appl. (1999), EP 869363 A1 19990107, Language: English, Database: CAPLUS 13. Preparation of water-soluble benzothiazolium-methine compound anticancer agents
By Tatsuta, Noriaki; Ikegawa, Akihiko; Kawakami, Masayuki; Koya, Keizo
From PCT Int. Appl. (1996), WO 9603393 A1 19960208, Language: English, Database: CAPLUS 14. Dimers of unsymmetrical cyanine dyes containing pyridinium moieties
By Yue, Stephen T.; Haugland, Richard P.

From U.S. (1995), U.S. Pat. No. 5,410,030 A 19950425, Language: English, Database: CAPLUS 15. Preparation of alkylsulfonate derivatives By Kawada, Ken From Jpn. Kokai Tokkyo Koho (1994), JP 06239845 A 19940630, Language: Japanese, Database: CAPLUS 16. preparation of quaternary salts of chalcogenites as photographic sensitizers By Yasumoto, Masahiko; Taguchi. Yoichi; Tsucha, Tooru; Tanaka, Mari From Jpn. Kokai Tokkyo Koho (1994), JP 06220026 A 19940809, Language: Japanese, Database: CAPLUS 17. High-sensitivity photosensitizers By Yamaoka, Tsugio; Koseki, Kenichi; Suga, Sadaji; Mitekura, Hirofumi; Yasui, Shigeo From Jpn. Kokai Tokkyo Koho (1994), JP 06107719 A 19940419, Language: Japanese, Database: CAPLUS 18. Preparation of azolioalkylsulfonates as dye intermediates By Kawata, Ken From U.S. (1994), U.S. Pat. No. 5,326,876 A 19940705, Language: English, Database: CAPLUS 19. Process for preparing sulfoalkyl-substituted heterocyclic quaternary ammonium salts By Vavrova, Jaroslava From Czech. (1993), CS 277581 B6 19930317, Language: Czech, Database: CAPLUS 20. Silver halide photographic material By Kawata, Ken; Ikeda, Tadashi From Eur. Pat. Appl. (1993), EP 565121 A1 19931013, Language: English, Database: CAPLUS 21. Preparation of N-substituted nitrogen-containing heterocyclic compounds By Kawada, Ken; Kato, Takashi From Jpn. Kokai Tokkyo Koho (1993), JP 05286954 A 19931102, Language: Japanese, Database: CAPLUS 22. Preparation of naphtho[1,2-d]thiazolinium-3-yl-alkanesulfonate and analogs as intermediates for dyes By Kawada, Ken From Jpn. Kokai Tokkyo Koho (1993), JP 05125066 A 19930521, Language: Japanese, Database: CAPLUS 23. Method for preparation of N-sulfoalkyl-substituted heterocyclic betaine salts as intermediates for polymethine dyes By Bach, Guenther; Eckert, Johanna From Ger. (East) (1990), DD 276787 A3 19900314, Language: German, Database: CAPLUS 24. Positive- or negative-working photosensitive lithographic plate, and fabrication of printing plate therefrom By Adachi, Yutaka; Goto, Sei; Nakai, Hideyuki; Tomiyasu, Hiroshi; Sasaki, Mitsuru From Jpn. Kokai Tokkyo Koho (1990), JP 02141754 A 19900531, Language: Japanese, Database: CAPLUS 25. Fluorescent merocyanines for photochemical inactivation of pathogenic viruses By Gunther, Wolfgang Hans Heinrich; Sauter, Frederick Joseph From PCT Int. Appl. (1989), WO 8912080 A1 19891214, Language: English, Database: CAPLUS 26. Photopolymerizable composition with initiator system containing sensitizer from methine compound By Nagasaka, Hedekl; Ohta, Katsuko From Eur. Pat. Appl. (1989), EP 300410 A2 19890125, Language: English, Database: CAPLUS 27. Preparation of benzothiazoles as intermediates for dyes, plant protectants and pharmaceuticals By Papenfuhs, Theodor From Ger. Offen. (1987), DE 3526032 A1 19870205, Language: German, Database: CAPLUS 28. Sulfoalkylthiazolium salts By Miura, Taketoshi; Tanaka, Akira From Jpn. Kokai Tokkyo Koho (1986), JP 61238773 A 19861024, Language: Japanese, Database: CAPLUS 29. Photographic photosensitive silver halide materials By Kohmura, Isao; Iwaosa, Katsuaki From Ger. Offen. (1984), DE 3403825 A1 19640816, Language: German, Database: CAPLUS 30. Sulfoalkyl quaternary salts of nitrogen-containing heterocyclic bases By Kampfer, Helmut; Himmelmann, Wolfgang From Ger. Offen. (1982), DE 3118374 A1 19821125, Language: German, Database: CAPLUS 31. Bis(3-sulfopropyl) ethers and their use as alkylating agents for organic bases By Kampfer, Helmut From Eur. Pat. Appl. (1982), EP 55428 A1 19820707, Language: German, Database: CAPLUS 32. Sulfoalkyl quaternary salts By Kampfer, Helmut; Hase, Marie; Glass, Max From Ger. Offen. (1979), DE 2803493 A1 19790802, Language: German, Database: CAPLUS 33. 2-Methylnaphthothiazoles By Kimura, Masaru; Morosawa, Shiro; Emoto, Takeo From Jpn. Kokai Tokkyo Koho (1979), JP 54019973 A 19790215, Language: Japanese, Database: CAPLUS 34. Photographic silver halide emulsions By Hinata, Masanao; Ohki, Masanaga; Ohi, Reiichi; Ogawa, Akira; Sato, Akira From Ger. Offen. (1975), DE 2458428 A1 19750612, Language: German, Database: CAPLUS 35. 2-Alkylthiazoles and 2-alkylselenazoles with attached aromatic rings By De Cat, Arthur H.; Manssens, Leo H.

From Belg. (1971), BE 758241 19710430, Language: French, Database: CAPLUS 36. 2-Methylbenzothiazoles, 2-methylbenzoselenazoles, and 2-methylnaphthothiazoles By De Cat, Arthur H.; Manssens, Leo H.

From Ger. Offer. (1971), DE 2053715 A 19710513, Language: German, Database: CAPLUS 37. o-Aminobenzenethiols by improved alkali fusion and benzothiazole derivatives By Horwitz, Lester; Clark, Charles A.

From No Corporate Source data available (1963), U.S. Pat. No. 3,102,142 19630827, Language: Unavailable, Database: CAPLUS 38. 2-Alkylnaphtho[1,2-d]thiazoles By Copeland, Ralph A.

From No Corporate Source data available (1960), U.S. Pat. No. 2,942,003 19600621, Language: Unavailable, Database: CAPLUS

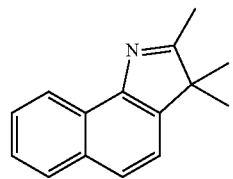 [SMILES: CC1=Nc2c(ccc3ccccc23)C1(C)C]

1. Binary cyanine dye for high speed DVD-R and its synthesis
By Su, Jianhua; Meng, Fanshun; Tian, He; Li, Cui; Wang, Hailong; Chen, Kongchang
From Faming Zhuanli Shenqing (2005), CN 1563201 A 20050112, Language: Chinese, Database: CAPLUS 2. Lightfast indoienine-type cyanine dyes, their intermediates, and optical recording media therewith
By Ono, Takao; Naruse, Shoichiro; Tsuchiya, Masahiro
From Jpn. Kokai Tokkyo Koho (2003), JP 2003171571 A 20030620, Language: Japanese, Database: CAPLUS 3. Photochromic plate containing specific photochromic compound as dummy wafer for semiconductor device fabrication
By Nakamura, Masataka
From Jpn. Kokai Tokkyo Koho (2002), JP 2002313695 A 20021025, Language: Japanese, Database: CAPLUS 4. Dye complex for recording layer of recordable optical disk
By Morishima, Shinichi; Usami, Takashi
From Eur. Pat. Appl. (2001), EP 1142961 A2 20011010, Language: English, Database: CAPLUS 5. Method for preparation of benzindolenine
By Asanuma, Naoki; Suzuki, Akira; Yamakawa, Kazuyoshi
From Jpn. Kokai Tokkyo Koho (2000), JP 2000128863 A 20000509, Language: Japanese, Database: CAPLUS 6. Preparation of spirooxazine fused to heterocyoles as photochromic compounds
By Yamamoto, Shinichi; Taniguchi, Takashi
From PCT Int. Appl. (1989), WO 8907104 A1 19890810, Language: Japanese, Database: CAPLUS 7. Preparation of spiro[benzoxazine-indoline, benzindoline, or piperidine] derivatives as photochromic substances
By Yamamoto, Shinichi; Taniguchi, Takashi
From Jpn. Kokai Tokkyo Koho (1989), JP 01052783 A 19890228, Language: Japanese, Database: CAPLUS 8. Preparation of spiro[oxazine-pyrrolidine] compounds as photochromic substances
By Yamamoto, Shinichi; Taniguchi, Takashi
From Jpn. Kokai Tokkyo Koho (1989), JP 01019081 A 19890123, Language: Japanese, Database: CAPLUS 9. Photochromic spiro(benzindolinonaphthoxazine) derivatives
By Nakajima, Mikito; Iriyo, Takeaki; Mogami, Takao
From Jpn. Kokai Tokkyo Koho (1988), JP 63267784 A 19881104, Language: Japanese, Database: CAPLUS 10. Photochromic compounds
By Kondo, Hirofumi; Arakawa, Seiichi; Seto, Nobuyoshi
From Jpn. Kokai Tokkyo Koho (1985), JP 60177089 A 19850911, Language: Japanese, Database: CAPLUS 11. Indolenines
By Laas, Harald; Nissan, Axel; Opgenorth, Hans Joachim; Scheuermann, Horst; Muelier, Hans Richard; Schulte, Wolfgang
From Ger. Offen. (1980), DE 2834607 A19800228, Language: German, Database: CAPLUS 1. Cyclometalated tricyclic benzofuro-, benzothio- and naphtho-annelated azole platinum-group metal complexes as phosphorescent compounds for electroluminescence devices with increased lifespan, efficiency and color purity
By Suh, Dong-Hack; Lim, Jin-Soo; Kim, Ji-Ho; Choi, Sun-Hyun
From PCT Int. Appl. (2007), WO 2007078184 A1 20070712, Language: English, Database: CAPLUS 2. Preparation of alkylsulfonate derivatives
By Kawada, Ken
From Jpn. Kokai Tokkyo Koho (1994), JP 06239845 A 19940830, Language: Japanese, Database: CAPLUS 3. preparation of quaternary salts of chalcogenites as photographic sensitizers
By Yasumoto, Masahiko; Taguchi, Yoichi; Tsucha, Tooru; Tanaka, Mari
From Jpn. Kokai Tokkyo Koho (1994), JP 06220028 A 19940809, Language: Japanese, Database: CAPLUS 4. Preparation of azolioalkylsulfonates as dye intermediates
By Kawata, Ken
From U.S. (1994), U.S. Pat. No. 5,326,876 A 19940705, Language: English, Database: CAPLUS 5. Preparation of naphtho[1,2-d]thiazolinium-3-yl-alkanesulfonate and analogs as intermediates for dyes
By Kawada, Ken
From Jpn. Kokai Tokkyo Koho (1993), JP 05125066 A 19930521, Language: Japanese, Database: CAPLUS 6. Fluorescent merocyanines for photochemical inactivation of pathogenic viruses
By Gunther, Wolfgang Hans Heinrich; Sauter, Frederick Joseph
From PCT Int. Appl. (1989), WO 8912080 A1 19891214, Language: English, Database: CAPLUS 7. Sulfoalkyl quaternary salts of nitrogen-containing heterocyclic bases
By Kampfer, Helmut; Himmelmann, Wolfgang
From Ger. Offen. (1962), DE 3118374 A1 19821125, Language: German, Database: CAPLUS 8. Bis(3-sulfopropyl) ethers and their use as alkylating agents for organic bases
By Kampfer, Helmut
From Eur. Pat. Appl. (1982), EP 55428 A1 19820707, Language: Garman, Database: CAPLUS 9. Alkylnaphthoxazoles
No inventor data available
From Jpn. Kokai Tokkyo Koho (1981), JP 56061368 A 19810526, Language: Japanese, Database: CAPLUS 10. Sulfoalkyl quaternary salts
By Kampfer, Helmut; Hase, Marie; Glass, Max
From Ger. Offen. (1979), DE 2803493 A1 19790802, Language: German, Database: CAPLUS 11. Propenium salts substituted with heterocycle
By Ciernkik, Jan; Vystavel, Vladislav
From Czech, (1973), CS 149322 B1 19730705, Language: Czech, Database: CAPLUS 12. Naphthoxazole dyes
By Okubo, Ichiro; Tsujimoto, Michihiro
From Jpn. Tokkyo Koho (1972), JP 47018913 B4 19720531, Language: Japanese, Database: CAPLUS

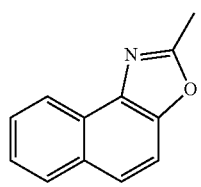

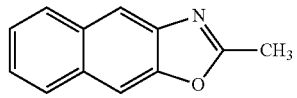

1. Tellurium compounds for protection from ultraviolet radiation
By Sredni, Benjamin; Albeck, Michael
From PCT Int. Appl. (2007), WO 2007032010 A2 20070322, Language: English, Database: CAPLUS 2. Reagents with bis-phenylarsine groups and procedures for high-specificity labeling
By Ebright, Richard H.; Ebright, Yon W.
From PCT Int. Appl. (2003), WO 2003107010 A1 20031224, Language: English, Database: CAPLUS 3. Bis-transition-metal-chelate-probes
By Ebright, Richard H.; Ebright, Yon W.
From PCT Int. Appl. (2003), WO 2003091689 A2 20031106, Language: English, Database: CAPLUS 4. Methine dye and silver halide photographic material
By Kobayashi, Masaru; Hio, Takanori
From Jpn. Kokai Tokkyo Koho (2001), JP 2001152038 A 20010605, Language: Japanese, Database: CAPLUS 5. Silver halide photographic materials with high sensitivity
By Kobayashi, Suguru
From Jpn. Kokai Tokkyo Koho (2001), JP 2001092068 A 20010406, Language: Japanese, Database: CAPLUS 6. Photographic emulsion containing novel sensitizing dye for silver halide emulsion in photographic materials
By Hioki, Takanori
From Jpn. Kokai Tokkyo Koho (2001), JP 2001081341 A 20010327, Language: Japanese, Database: CAPLUS 7. Methine dyes containing sulfo-substituted aromatic groups for photographic sensitizers and their manufacture
By Kobayashi, Suguru
Form Jpn. Kokai Tokkyo Koho (2001), JP 2001064528 A 20010313, Language: Japanese, Database: CAPLUS 8. High sensitive silver halide enulsion and silver halide photographic material using the same
By Kobayashi, Suguru
From Jpn. Kokai Tokkyo Koho (2000), JP 2000081680 A 20000321, Language: Japanese, Database: CAPLUS 9. Sultone compounds, quaternary ammonium and methine compounds thereof, their manufacture, and silver halide photographic materials containing them
By Hioki, Takanori
From Jpn. Kokai Tokkyo Koho (1998), JP 10168330 A 19960623, Language: Japanese, Database: CAPLUS 10. Fluorescent merocyanines for photochemical inactivation of pathogenic viruses
By Gunther, Wolfgang Hans Heinrich; Sauter, Frederick Joseph
From PCT Int. Appl. (1989), WO 8912080 A1 19891214, Language: English, Database: CAPLUS 11. 2-Methylaryloxazoles
By Matsuo, Masatoshi; Muroyama, Yuzo
From Jpn. Kokai Tokkyo Koho (1974), JP 49031662 A 19740322, Language: Japanese, Database: CAPLUS

APPENDIX B

| Naphtho[1,2-d]oxazol-2-amine Derivatives | | Naphtho[2,1-d]oxazol-2-amine Derivatives | |
|---|---|---|---|
| Structure | Name | Structure | Name |
| (structure) | 5-methylnaphtho[1,2-d]oxazol-2-amine | (structure) | 5-methylnaphtho[2,1-d]oxazol-2-2-amine |
| (structure) | 5-ethylnaphtho[1,2-d]oxazol-2-amine | (structure) | 5-ethylnaphtho[2,1-d]oxazol-2-amine |
| (structure) | 5-propylnaphtho[1,2-d]oxazol-2-amine | (structure) | 5-propylnaphtho[2,1-d]oxazol-2-amine |

| Naphtho[1,2-d]oxazol-2-amine Derivatives | | Naphtho[2,1-d]oxazol-2-amine Derivatives | |
|---|---|---|---|
| Structure | Name | Structure | Name |
| | 5-cyclopropylnaphtho[1,2-d]oxazol-2-amine | | 5-cyclopropylnaphtho[2,1-d]oxazol-2-amine |
| | 5-(tert-butyl)naphtho[1,2-d]oxazol-2-amine | | 5-(tert-butyl)naphtho[2,1-d]oxazol-2-amine |
| | 5-fluoronaphtho[1,2-d]oxazol-2-amine | | 5-fluoronaphtho[2,1-d]oxazol-2-amine |
| | 5-chloronaphtho[1,2-d]oxazol-2-amine | | 5-chloronaphtho[2,1-d]oxazol-2-amine |
| | 5-bromonaphtho[1,2-d]oxazol-2-amine | | 5-bromonaphtho[2,1-d]oxazol-2-amine |
| | 5-iodonaphtho[1,2-d]oxazol-2-amine | | 5-iodonaphtho[2,1-d]oxazol-2-amine |

-continued

| Naphtho[1,2-d]oxazol-2-amine Derivatives | | Naphtho[2,1-d]oxazol-2-amine Derivatives | |
|---|---|---|---|
| Structure | Name | Structure | Name |
| | 2-aminonaphtho[1,2-d]oxazole-5-carbonitrile | | 2-aminonaphtho[2,1-d]oxazole-5-carbonitrile |
| | naphtho[1,2-d]oxazole-2,5-diamine | | naphtho[2,1-d]oxazole-2,5-diamine |
| | $N^5$-methylnaphtho[1,2-d]oxazole-2,5-diamine | | $N^5$-methylnaphtho[2,1-d]oxazole-2,5-diamine |
| | $N^5,N^5$-dimethylnaphtho[1,2-d]oxazole-2,5-diamine | | $N^5,N^5$-dimethylnaphtho[2,1-d]oxazole-2,5-diamine |
| | $N^5$-methylnaphtho[1,2-d]oxazole-2,5-diamine | | $N^5$-methylnaphtho[2,1-d]oxazole-2,5-diamine |
| | 5-(pyrrolidin-1-yl)naphtho[1,2-d]oxazol-2-amine | | 5-(pyrrolidin-1-yl)naphtho[2,1-d]oxazol-2-amine |

| Naphtho[1,2-d]oxazol-2-amine Derivatives | | Naphtho[2,1-d]oxazol-2-amine Derivatives | |
|---|---|---|---|
| Structure | Name | Structure | Name |
| | 5-methoxynaphtho[1,2-d]oxazol-2-amine | | 5-methoxynaphtho[2,1-d]oxazol-2-amine |
| | 5-trifluoromethylnaphtho[1,2-d]oxazol-2-amine | | 5-fluoromethylnaphtho[2,1-dioxazol-2-amine |

What is claimed is:

1. A composition of matter comprising:

R-[1,2-d]oxazol-2-amine wherein R is selected from: 5-methylnaptho; 5-ethylnaphtho; 5-propylnaphtho; 5-cyclopropylnaphtho; 5-(tert-butyl)naphtha; 5-fluoronaphtho; 5-chloronaphtho; 5-bromonaphtho; and 5-iodonaphtho.

2. A composition of matter according to claim 1, wherein the composition comprises 2-aminonaphtho[1,2-d]oxazole-5-carbonitrile.

3. A composition of matter according to claim 1, wherein the composition comprises naphtho[1,2-d]oxazole-2,5-diamine.

4. A composition of matter according to claim 1, wherein the composition comprises $N^5$-methylnaphtho[1,2-d]oxazole-2,5-diamine.

5. A composition of matter according to claim 1, wherein the composition comprises $N^5,N^5$-dimethylnaphtho[1,2-d]oxazole-2,5-diamine.

6. A composition of matter according to claim 1, wherein the composition comprises $N^5$-ethylnaphtho[1,2-d]oxazole-2,5-diamine.

7. A composition of matter according to claim 1, wherein the composition comprises 5-(pyrrolidin-1-yl)naphtho[1,2-d]oxazol-2-amine.

8. A composition of matter according to claim 1, wherein the composition comprises 5-methylnaphtho[2,1-d]oxazol-2-amine.

9. A composition of matter according to claim 1, wherein the composition comprises 5-trifluoromethylnaphtho[1,2-d]oxazol-2-amine.

10. A composition of matter comprising:

R-[1,2-d]oxazol-2-amine wherein R is selected from: 5-ethylnaphtho; 5-propylnaphtho; 5-cyclopropylnaphtho; 5-(tert-butyl)naphtha; 5-fluoronaphtho; 5-chloronaphtho; 5-romonaphtho; and 5-iodonaphtho.

11. A composition of matter according to claim 10, wherein the composition comprises 2-aminonaphtho[2,1-d]oxazole-5-carbonitrile.

12. A composition of matter according to claim 10, wherein the composition comprises naphtho[2,1-d]oxazole-2,5-diamine.

13. A composition of matter according to claim 10, wherein the composition comprises $N^5$-methylnaphtho[2,1-d]oxazole-2,5-diamine.

14. A composition of matter according to claim 10, wherein the composition comprises $N^5,N^5$-dimethylnaphtho[2,1-d]oxazole-2,5-diamine.

15. A composition of matter according to claim 10, wherein the composition comprises $N^5$-ethylnaphtho[1,2-d]oxazole-2,5-diamine.

16. A composition of matter according to claim 10, wherein the composition comprises 5-(pyrrolidin-1-yl)naphtho[2,1-d]oxazol-2-amine.

17. A composition of matter according to claim 10, wherein the composition comprises 5-methoxynaphtho[2,1-d]oxazol-2-amine.

18. A composition of matter according to claim 10, wherein the composition comprises 5-trifluoromethylnaphtho[2,1-d]oxazol-2-amine.

* * * * *